United States Patent
Nakahara et al.

(10) Patent No.: US 11,883,999 B2
(45) Date of Patent: Jan. 30, 2024

(54) SYNTHETIC POLYMER FILM PROVIDED WITH SURFACE HAVING STERILIZING EFFECT, METHOD FOR MANUFACTURING SYNTHETIC POLYMER FILM AND STERILIZATION METHOD USING SURFACE OF SYNTHETIC POLYMER FILM

(71) Applicant: SHARP KABUSHIKI KAISHA, Sakai (JP)

(72) Inventors: Takahiro Nakahara, Sakai (JP); Hidekazu Hayashi, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 281 days.

(21) Appl. No.: 15/760,797

(22) PCT Filed: Aug. 24, 2016

(86) PCT No.: PCT/JP2016/074675
§ 371 (c)(1),
(2) Date: Mar. 16, 2018

(87) PCT Pub. No.: WO2017/047344
PCT Pub. Date: Mar. 23, 2017

(65) Prior Publication Data
US 2018/0257329 A1 Sep. 13, 2018

(30) Foreign Application Priority Data
Sep. 17, 2015 (JP) .................................. 2015-183998

(51) Int. Cl.
*A61L 2/00* (2006.01)
*A61L 9/00* (2006.01)
(Continued)

(52) U.S. Cl.
CPC .............. *B29C 59/046* (2013.01); *A61L 2/00* (2013.01); *A61L 2/232* (2013.01); *A61L 9/00* (2013.01);
(Continued)

(58) Field of Classification Search
CPC ........... B82Y 30/00; B82Y 5/00; B82Y 20/00; B82B 3/00; B82B 3/0009; B82B 3/0014;
(Continued)

(56) References Cited

U.S. PATENT DOCUMENTS 9,781,924 B2    10/2017    Yamada et al.
9,781,925 B2    10/2017    Yamada et al.
(Continued)

FOREIGN PATENT DOCUMENTS

CN      201329050 Y    10/2009
JP       H08-24843 A     1/1996
(Continued)

OTHER PUBLICATIONS

Machine translation (Espacenet) of JP 2005-048135 A. Translated May 22, 2020. (Year: 2020).*
(Continued)

*Primary Examiner* — Maria V Ewald
*Assistant Examiner* — Ethan A. Utt
(74) *Attorney, Agent, or Firm* — ScienBiziP, P.C.

(57) ABSTRACT

A synthetic polymer film (35), (36) having a surface which has a plurality of raised portions (35p), (36p), wherein a two-dimensional size of the plurality of raised portions is in a range of more than 20 nm and less than 500 nm when viewed in a normal direction of the synthetic polymer film, the surface having a microbicidal effect, and the synthetic polymer film includes a fluorine element in such a profile that a fluorine content is not constant in a thickness direction but is higher in a portion closer to the plurality of raised (Continued)

portions than in a portion farther from the plurality of raised portions.

21 Claims, 11 Drawing Sheets

(51) Int. Cl.
| | |
|---|---|
| B32B 27/00 | (2006.01) |
| C08J 7/04 | (2020.01) |
| B32B 3/30 | (2006.01) |
| C08J 5/18 | (2006.01) |
| B82Y 30/00 | (2011.01) |
| C08F 20/06 | (2006.01) |
| B29C 59/04 | (2006.01) |
| C08L 75/16 | (2006.01) |
| C09D 4/00 | (2006.01) |
| C08J 7/043 | (2020.01) |
| C08J 7/046 | (2020.01) |
| A61L 2/232 | (2006.01) |
| B32B 15/095 | (2006.01) |
| C08L 75/14 | (2006.01) |
| B82Y 40/00 | (2011.01) |
| B29C 35/08 | (2006.01) |
| B29C 59/02 | (2006.01) |

(52) U.S. Cl.
CPC ............ *B32B 3/30* (2013.01); *B32B 15/095* (2013.01); *B32B 27/00* (2013.01); *C08J 5/18* (2013.01); *C08J 7/042* (2013.01); *C08J 7/043* (2020.01); *C08J 7/046* (2020.01); *C08J 7/0423* (2020.01); *C08J 7/0427* (2020.01); *C08L 75/14* (2013.01); *C08L 75/16* (2013.01); *C09D 4/00* (2013.01); *B29C 2035/0827* (2013.01); *B29C 2059/023* (2013.01); *B82Y 30/00* (2013.01); *B82Y 40/00* (2013.01); *C08F 20/06* (2013.01); *C08J 2427/12* (2013.01); *C08J 2433/06* (2013.01); *C08J 2475/16* (2013.01); *C08L 2203/16* (2013.01)

(58) Field of Classification Search
CPC ......... B82B 3/0033; B82B 1/00; B82B 1/008; Y10T 428/24355; Y10T 428/24479; Y10T 428/24612; Y10T 428/3154; Y10T 428/31551; Y10T 428/31565; Y10T 428/31573; Y10T 428/31576; Y10T 428/31583; Y10T 428/31591; Y10T 428/31598; Y10T 428/31616; Y10T 428/3162; Y10T 428/31855; Y10T 428/3188; Y10T 428/31884; Y10T 428/31891; Y10T 428/31935; Y10T 428/31663; Y10T 428/31667; Y10T 428/24942; Y10T 428/31; Y10T 428/31544; Y10T 428/31909; B32B 3/00; B32B 3/26; B32B 3/30; B32B 9/00; B32B 9/04; B32B 9/045; B32B 27/00; B32B 27/06; B32B 27/08; B32B 27/16; B32B 27/18; B32B 27/30; B32B 27/308; B32B 27/40; B32B 2551/00; B32B 3/263; B32B 7/00; B32B 7/02; B32B 2535/00; B32B 2457/20; B32B 2457/202; B32B 2457/204; B32B 2457/206; B32B 2457/208; G02B 1/00; G02B 1/04; G02B 1/10; G02B 1/11; G02B 1/111; G02B 1/118; G02B 1/12; G02B 1/18; G02B 2207/00; G02B 2207/101; A01N 25/00; A01N 25/34; A01N 33/00; A01N 33/02; A01N 33/04; A01N 33/06; A01N 33/08; A01N 33/10; A01N 33/12; A01N 33/14; A01N 33/16; A01N 33/18; A01N 33/20; A01N 33/22; A01N 33/24; A01N 33/26; Y10S 977/70; Y10S 977/778; Y10S 977/782; Y10S 977/783; Y10S 977/788; Y10S 977/789; Y10S 977/832; Y10S 977/834; Y10S 977/835; Y10S 977/836; Y10S 977/904; Y10S 977/932; Y10S 977/952
USPC ....... 977/700, 762, 788, 789, 809, 832, 840, 977/887, 888, 890–892, 902–904, 778, 977/782, 783, 834–836, 932, 952; 428/141, 156, 172, 421, 423.1, 423.7, 428/424.2–424.7, 425.1, 425.5, 480, 481, 428/500, 507, 508, 510, 522, 451, 428/446–448, 212, 409, 422, 515, 520; 359/601
See application file for complete search history.

(56) References Cited

U.S. PATENT DOCUMENTS

| | | | |
|---|---|---|---|
| 9,781,926 B2 | 10/2017 | Yamada et al. | |
| 2003/0205475 A1 | 11/2003 | Sawitowski | |
| 2007/0159698 A1 | 7/2007 | Taguchi et al. | |
| 2010/0203161 A1 | 8/2010 | Gehri et al. | |
| 2011/0128629 A1* | 6/2011 | Takahashi | G02B 1/18 359/601 |
| 2011/0235181 A1 | 9/2011 | Hayashibe et al. | |
| 2011/0281068 A1 | 11/2011 | David et al. | |
| 2012/0318772 A1 | 12/2012 | Minoura et al. | |
| 2013/0057958 A1 | 3/2013 | Minoura et al. | |
| 2013/0071646 A1* | 3/2013 | Kim | G02B 1/111 428/323 |
| 2013/0078440 A1* | 3/2013 | Kim | G02B 1/115 428/212 |
| 2013/0129977 A1* | 5/2013 | Takihara | G02B 1/118 428/141 |
| 2013/0210957 A1* | 8/2013 | Takihara | C08F 220/22 522/182 |
| 2014/0077418 A1 | 3/2014 | Otani et al. | |
| 2015/0140154 A1 | 5/2015 | Tsurugi et al. | |
| 2015/0168610 A1 | 6/2015 | Fukui et al. | |
| 2015/0273755 A1 | 10/2015 | Yee et al. | |
| 2016/0113274 A1 | 4/2016 | Yamada et al. | |
| 2016/0121005 A1 | 5/2016 | Nakahara et al. | |
| 2016/0212989 A1 | 7/2016 | Juodkazis et al. | |
| 2017/0066207 A1 | 3/2017 | Hayashi et al. | |
| 2017/0238539 A1 | 8/2017 | Yamada et al. | |
| 2017/0258081 A1 | 9/2017 | Yamada et al. | |
| 2017/0320281 A1 | 11/2017 | Hayashi et al. | |
| 2018/0035668 A1 | 2/2018 | Yamada et al. | |

FOREIGN PATENT DOCUMENTS

| | | | |
|---|---|---|---|
| JP | 2000301053 A | * | 10/2000 |
| JP | 2005048135 A | * | 2/2005 |
| JP | 2005-055114 A | | 3/2005 |
| JP | 2008-197217 A | | 8/2008 |
| JP | 4265729 B2 | | 5/2009 |
| JP | 2009-166502 A | | 7/2009 |
| JP | 2010-000719 A | | 1/2010 |
| JP | 2010-079200 A | | 4/2010 |
| JP | 2010-201799 A | | 9/2010 |
| JP | 2011178910 A | * | 9/2011 |
| JP | 2012-078438 A | | 4/2012 |
| JP | 2012-514239 A | | 6/2012 |
| JP | 2013-033287 A | | 2/2013 |
| JP | 2013-078573 A | | 5/2013 |
| JP | 2014-029391 A | | 2/2014 |
| JP | 2014-066975 A | | 4/2014 |
| JP | 2014-153684 A | | 8/2014 |

(56) References Cited

FOREIGN PATENT DOCUMENTS

| JP | 2014-188852 A | | 10/2014 | | |
|---|---|---|---|---|---|
| JP | 2014-202955 A | | 10/2014 | | |
| JP | 2014188852 A | * | 10/2014 | | |
| JP | 2015-024549 A | | 2/2015 | | |
| JP | 5788128 B1 | | 9/2015 | | |
| JP | 2016-026546 A | | 2/2016 | | |
| JP | 2016-093939 A | | 5/2016 | | |
| JP | 2016-104545 A | | 6/2016 | | |
| JP | 5951165 B1 | | 7/2016 | | |
| WO | 2011/125486 A1 | | 10/2011 | | |
| WO | 2011/148721 A1 | | 12/2011 | | |
| WO | 2013/183576 A1 | | 12/2013 | | |
| WO | 2013/191092 A1 | | 12/2013 | | |
| WO | 2014/021376 A1 | | 2/2014 | | |
| WO | 2014/171365 A1 | | 10/2014 | | |
| WO | WO-2015031956 A1 | * | 3/2015 | ............. | A01N 25/34 |
| WO | 2015/166725 A1 | | 11/2015 | | |
| WO | 2016/080245 A1 | | 5/2016 | | |
| WO | 2016/208540 A1 | | 12/2016 | | |

OTHER PUBLICATIONS

Buschow, K.H., et al. (2001). Encyclopedia of Materials—Science and Technology, vols. 1-11—Polyurethanes in Biomedical Engineering. Elsevier. Retrieved from app.knovel.com/hotlink/pdf/id:kt00B7AMYB/encyclopedia-materials/polyurethanes-in-biomedical (Year: 2001).*

Machine translation (Espacenet) of JP 2011-178910 A. Translated Jul. 17, 2021. (Year: 2021).*

Machine translation (Espacenet) of JP 2000-301053 A. Translated Feb. 6, 2023. (Year: 2023).*

Machine translation (Espacenet) of JP 2014-188852 A. Translated Feb. 11, 2023. (Year: 2023).*

Sergey Pogodin et al. "Biophysical model of bacterial cell interactions with nanopatterned cicada wing surfaces." Biophysical Journal vol. 104 Feb. 2013 p. 835-840.

Co-pending letter for related co-pending U.S. Appl. No. 14/771,833, U.S. Appl. No. 15/386,131, U.S. Appl. No. 15/437,044, U.S. Appl. No. 15/592,922, U.S. Appl. No. 15/784,771, U.S. Appl. No. 14/897,252, U.S. Appl. No. 15/126,078, U.S. Appl. No. 15/739,450, U.S. Appl. No. 15/118,536, U.S. Appl. No. 15/649,755.

Office Action dated Dec. 29, 2016 issued in the related U.S. Appl. No. 14/771,833.

Office Action dated Oct. 27, 2016 issued in the related U.S. Appl. No. 14/771,833.

E.P. Ivanova et al., "Bactericidal activity of black silicon", Nature Communications, Published Nov. 26, 2013, 19pgs, Macmillan Publishers Limited.

Epstein, A.K. et al. "Liquid-infused structured surfaces with exceptional anti-biofouling performances," PNAS, Aug. 14, 2012, vol. 109, No. 33.

Yao, C. et al. "Decreased bacteria density on nanostructured polyurethane," Society for Biomaterials, pp. 1823-1828, Jun. 29, 2013.

Ivanova, E. et al., "Natural Bactericidal Surfaces: Mechanical Repture of Pseudomonas aeruginosa Cells by Cicada Wings," Small Journal, pp. 1-6, 2012.

Trafton, A., (2006) "MIT's Anti-Microbial "Paint" Kills Flu, Bacteria" http://chemistry.mit.edu/mitsanti-microbial-paint-kills-flu-bacteria, p. 2-4.

Good Housekeeping (2011) "Do-It-All Cleaning Guide" http://www.goodhousekeeping.com/home/cleaning/tips/a18875/how-to-clean/, p. 1-12.

Office Action dated Mar. 9, 2017 issued in U.S. Appl. No. 15/386,131.

* cited by examiner (a)

(b)

(a)

(b)

(c)

(d)

(e)

(a)

(b)

(c)

(a)

(b)

(c)

(a)

(b)

(c)

(a)

1.00μm (b)

500nm (a)

(b)

SYNTHETIC POLYMER FILM PROVIDED WITH SURFACE HAVING STERILIZING EFFECT, METHOD FOR MANUFACTURING SYNTHETIC POLYMER FILM AND STERILIZATION METHOD USING SURFACE OF SYNTHETIC POLYMER FILM

TECHNICAL FIELD

The present invention relates to a synthetic polymer film whose surface has a microbicidal activity, a method for producing a synthetic polymer film, a sterilization method with the use of the surface of the synthetic polymer film, a mold for production of the synthetic polymer film, and a mold manufacturing method. In this specification, the "mold" includes molds that are for use in various processing methods (stamping and casting), and is sometimes referred to as a stamper. The "mold" can also be used for printing (including nanoimprinting).

BACKGROUND ART

Recently, it was reported that surficial nanostructures of black silicon, wings of cicadas and dragonflies have a bactericidal activity (Non-patent Document 1). Reportedly, the physical structure of the nanopillars that black silicon and wings of cicadas and dragonflies have produces a bactericidal activity.

According to Non-patent Document 1, black silicon has the strongest bactericidal activity on Gram-negative bacteria, while wings of dragonflies have a weaker bactericidal activity, and wings of cicadas have a still weaker bactericidal activity. Black silicon has 500 nm tall nanopillars. Wings of cicadas and dragonflies have 240 nm tall nanopillars. The static contact angle (hereinafter, sometimes simply referred to as "contact angle") of the black silicon surface with respect to water is 80°, while the contact angles of the surface of wings of dragonflies and cicadas with respect to water are 153° and 159°, respectively. It is estimated that black silicon is mainly made of silicon, and wings of dragonflies and cicadas are made of chitin. According to Non-patent Document 1, the composition of the surface of black silicon is generally a silicon oxide, and the composition of the surface of wings of dragonflies and cicadas is generally a lipid.

CITATION LIST

Patent Literature

Patent Document 1: Japanese Patent No. 4265729
Patent Document 2: Japanese Laid-Open Patent Publication No. 2009-166502
Patent Document 3: WO 2011/125486
Patent Document 4: WO 2013/183576

Non-Patent Literature

Non-patent Document 1: Ivanova, E. P. et al., "Bactericidal activity of black silicon", Nat. Commun. 4:2838 doi: 10.1038/ncomms3838 (2013).

SUMMARY OF INVENTION

Technical Problem

The mechanism of killing bacteria by nanopillars is not clear from the results described in Non-patent Document 1. It is also not clear whether the reason why black silicon has a stronger bactericidal activity than wings of dragonflies and cicadas resides in the difference in height or shape of nanopillars, in the difference in surface free energy (which can be evaluated by the contact angle), in the materials that constitute nanopillars, or in the chemical properties of the surface.

The bactericidal activity of black silicon is difficult to utilize because black silicon is poor in mass productivity, and is hard but brittle so that the shapability is poor.

The present invention was conceived for the purpose of solving the above problems. The major objects of the present invention include providing a synthetic polymer film whose surface has a microbicidal activity, a method for producing a synthetic polymer film, a sterilization method with the use of the surface of the synthetic polymer film, a mold for production of the synthetic polymer film, and a mold manufacturing method. The objects of the present invention further include providing a synthetic polymer film whose surface has a microbicidal activity and in which grease, such as fingerprint, adhered to the surface is inconspicuous, a method for producing a synthetic polymer film, and a sterilization method with the use of the surface of the synthetic polymer film.

Solution to Problem

A synthetic polymer film according to an embodiment of the present invention has a surface which has a plurality of raised portions, wherein a two-dimensional size of the plurality of raised portions is in a range of more than 20 nm and less than 500 nm when viewed in a normal direction of the synthetic polymer film, the surface having a microbicidal effect, and the synthetic polymer film includes a fluorine element in such a profile that a fluorine content is not constant in a thickness direction but is higher in a portion closer to the plurality of raised portions than in a portion farther from the plurality of raised portions.

In one embodiment, the synthetic polymer film includes a first resin film and a second resin film provided on the first resin film, the second resin film including a fluorine-containing mold releasing agent, wherein a fluorine content of the first resin film and a fluorine content of the second resin film are each constant in the thickness direction, and the fluorine content of the second resin film is higher than the fluorine content of the first resin film.

In one embodiment, the synthetic polymer film further includes an oxide film interposed between the first resin film and the second resin film, wherein the fluorine-containing mold releasing agent includes alkoxysilane.

In one embodiment, the fluorine content continuously varies in the thickness direction.

In one embodiment, a portion of the synthetic polymer film which includes the fluorine element is made of a fluorine-containing acrylic resin and a resin which includes an acryloyl group.

In one embodiment, a nitrogen content continuously varies in the thickness direction.

In one embodiment, the synthetic polymer film includes, at a surface opposite to the surface, a nitrogen element (exclusive of a nitrogen element which is a constituent of a tertiary amine) in the proportion of not less than 0.430 at %.

In one embodiment, the synthetic polymer film includes, at a surface opposite to the surface, a nitrogen element (exclusive of a nitrogen element which is a constituent of a tertiary amine) in the proportion of not less than 1.035 at %.

In one embodiment, the synthetic polymer film includes a urethane acrylate structure.

A synthetic polymer film production method according to an embodiment of the present invention is a method for producing a synthetic polymer film using a mold which includes a porous alumina layer, the porous alumina layer having an inverted moth-eye structure over its surface, the inverted moth-eye structure including a plurality of recessed portions whose two-dimensional size viewed in a normal direction of the surface is not less than 20 nm and less than 500 nm, the method including: (a) providing the mold and a work; (b) irradiating a first resin, which is a UV-curable resin, interposed between the mold and a surface of the work with ultraviolet light, thereby curing the first resin; and (c) providing a second resin on the cured first resin, the second resin including a fluorine-containing mold releasing agent.

In one embodiment, the method further includes, before (c), forming an oxide film on the cured first resin, wherein the fluorine-containing mold releasing agent includes alkoxysilane.

A synthetic polymer film production method according to another embodiment of the present invention is a method for producing a synthetic polymer film using a mold which includes a porous alumina layer, the porous alumina layer having an inverted moth-eye structure over its surface, the inverted moth-eye structure including a plurality of recessed portions whose two-dimensional size viewed in a normal direction of the surface is not less than 20 nm and less than 500 nm, the method comprising: (a) providing the mold and a work; (b) applying a first resin, which is a UV-curable resin, to a surface of the work and applying a second resin including a fluorine-containing monomer to a surface of the mold; and (c) irradiating, with ultraviolet light, the first resin and the second resin which are interposed between the mold and the surface of the work so as to be in contact with each other, thereby curing the first resin and the second resin.

In one embodiment, the second resin further includes a reactive diluent but does not include a solvent.

In one embodiment, the first resin includes a nitrogen element (exclusive of a nitrogen element which is a constituent of a tertiary amine) in the proportion of not less than 0.430 at %.

In one embodiment, the first resin includes a nitrogen element (exclusive of a nitrogen element which is a constituent of a tertiary amine) in the proportion of not less than 1.035 at %.

In one embodiment, the first resin includes a urethane acrylate structure.

A method for sterilizing a gas or liquid according to an embodiment of the present invention includes bringing the gas or liquid into contact with the surface of the synthetic polymer film as set forth in any of the foregoing paragraphs or a surface of a synthetic polymer film produced by the method as set forth in any of the foregoing paragraphs.

Advantageous Effects of Invention

According to an embodiment of the present invention, a synthetic polymer film whose surface has a microbicidal activity, a method for producing a synthetic polymer film, a sterilization method with the use of the surface of the synthetic polymer film, a mold for production of the synthetic polymer film, and a mold manufacturing method are provided. According to another embodiment of the present invention, a synthetic polymer film whose surface has a microbicidal activity and in which grease, such as fingerprint, adhered to the surface is inconspicuous, a method for producing a synthetic polymer film, and a sterilization method with the use of the surface of the synthetic polymer film are provided.

DESCRIPTION OF EMBODIMENTS

Hereinafter, a synthetic polymer film whose surface has a microbicidal effect, a sterilization method with the use of the surface of the synthetic polymer film, a mold for production of the synthetic polymer film, and a mold manufacturing method according to embodiments of the present invention are described with reference to the drawings.

In this specification, the following terms are used.

"Sterilization" (or "microbicidal") means reducing the number of proliferative microorganisms contained in an object, such as solid or liquid, or a limited space, by an effective number.

"Microorganism" includes viruses, bacteria, and fungi.

"Antimicrobial" generally includes suppressing and preventing multiplication of microorganisms and includes suppressing dinginess and slime which are attributed to microorganisms.

The present applicant conceived a method for producing an antireflection film (an antireflection surface) which has a moth-eye structure with the use of an anodized porous alumina layer. Using the anodized porous alumina layer enables manufacture of a mold which has an inverted moth-eye structure with high mass-productivity (e.g., Patent Documents 1 to 4). The entire disclosures of Patent Documents 1 to 4 are incorporated by reference in this specification.

The present inventors developed the above-described technology and arrived at the concept of a synthetic polymer film whose surface has a microbicidal effect.

Figure 1:
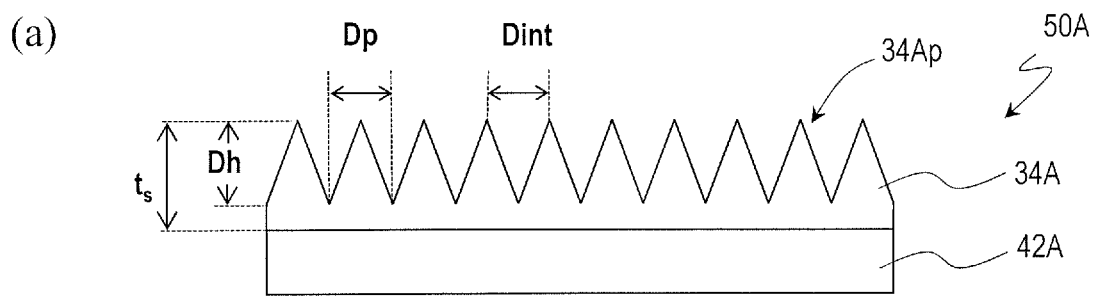
FIGS. 1(a) and 1(b) are schematic cross-sectional views of synthetic polymer films 34A and 34B, respectively, according to embodiments of the present invention.
Figure 1:
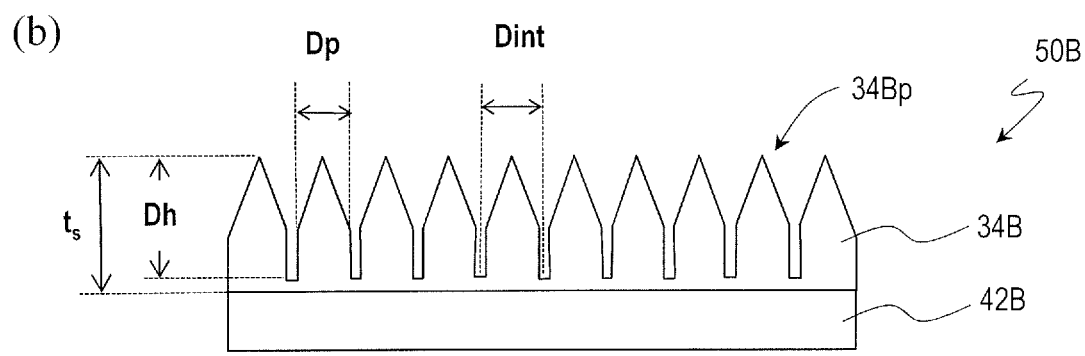

The configuration of a synthetic polymer film according to an embodiment of the present invention is described with reference to FIGS. 1(a) and 1(b).

FIGS. 1(a) and 1(b) respectively show schematic cross-sectional views of synthetic polymer films 34A and 34B according to embodiments of the present invention. The synthetic polymer films 34A and 34B described herein as examples are formed on base films 42A and 42B, respectively, although the present invention is not limited to these examples. The synthetic polymer films 34A and 34B can be directly formed on a surface of an arbitrary object.

A film 50A shown in FIG. 1(a) includes a base film 42A and a synthetic polymer film 34A provided on the base film 42A. The synthetic polymer film 34A has a plurality of raised portions 34Ap over its surface. The plurality of raised portions 34Ap constitute a moth-eye structure. When viewed in a normal direction of the synthetic polymer film 34A, the two-dimensional size of the raised portions 34Ap, $D_p$, is in the range of more than 20 nm and less than 500 nm. Here, the "two-dimensional size" of the raised portions 34Ap refers to the diameter of a circle equivalent to the area of the raised portions 34Ap when viewed in a normal direction of the surface. When the raised portions 34Ap have a conical shape, for example, the two-dimensional size of the raised portions 34Ap is equivalent to the diameter of the base of the cone. The typical adjoining distance of the raised portions 34Ap, $D_{int}$, is more than 20 nm and not more than 1000 nm. When the raised portions 34Ap are densely arranged so that there is no gap between adjoining raised portions 34Ap (e.g., the bases of the cones partially overlap each other) as shown in FIG. 1(a), the two-dimensional size of the raised portions 34Ap, $D_p$, is equal to the adjoining distance $D_{int}$. The typical height of the raised portions 34Ap, $D_h$, is not less than 50 nm and less than 500 nm. As will be described later, a microbicidal activity is exhibited even when the height $D_h$ of the raised portions 34Ap is not more than 150 nm. The thickness of the synthetic polymer film 34A, $t_s$, is not particularly limited but only needs to be greater than the height $D_h$ of the raised portions 34Ap.

The synthetic polymer film 34A shown in FIG. 1(a) has the same moth-eye structure as the antireflection films disclosed in Patent Documents 1 to 4. From the viewpoint of producing an antireflection function, it is preferred that the surface has no flat portion, and the raised portions 34Ap are densely arranged over the surface. Further, the raised portions 34Ap preferably has a such shape that the cross-sectional area (a cross section parallel to a plane which is orthogonal to an incoming light ray, e.g., a cross section parallel to the surface of the base film 42A) increases from the air side to the base film 42A side, e.g., a conical shape.

From the viewpoint of suppressing interference of light, it is preferred that the raised portions 34Ap are arranged without regularity, preferably randomly. However, these features are unnecessary when only the microbicidal activity of the synthetic polymer film 34A is pursued. For example, the raised portions 34Ap do not need to be densely arranged. The raised portions 34Ap may be regularly arranged. Note that, however, the shape and arrangement of the raised portions 34Ap are preferably selected such that the raised portions 34Ap effectively act on microorganisms.

A film 50B shown in FIG. 1(b) includes a base film 42B and a synthetic polymer film 34B provided on the base film 42B. The synthetic polymer film 34B has a plurality of raised portions 34Bp over its surface. The plurality of raised portions 34Bp constitute a moth-eye structure. In the film 50B, the configuration of the raised portions 34Bp of the synthetic polymer film 34B is different from that of the raised portions 34Ap of the synthetic polymer film 34A of the film 50A. Descriptions of features which are common with those of the film 50A are sometimes omitted.

When viewed in a normal direction of the synthetic polymer film 34B, the two-dimensional size of the raised portions 34Bp, $D_p$, is in the range of more than 20 nm and less than 500 nm. The typical adjoining distance of the raised portions 34Bp, $D_{int}$, is more than 20 nm and not more than 1000 nm, and $D_p < D_{int}$ holds. That is, in the synthetic polymer film 34B, there is a flat portion between adjoining raised portions 34Bp. The raised portions 34Bp have the shape of a cylinder with a conical portion on the air side. The typical height of the raised portions 34Bp, $D_h$, is not less than 50 nm and less than 500 nm. The raised portions 34Bp may be arranged regularly or may be arranged irregularly. When the raised portions 34Bp are arranged regularly, $D_{int}$ also represents the period of the arrangement. This also applies to the synthetic polymer film 34A, as a matter of course.

In this specification, the "moth-eye structure" includes not only surficial nanostructures that have an excellent antireflection function and that are formed by raised portions which have such a shape that the cross-sectional area (a cross section parallel to the film surface) increases as do the raised portions 34Ap of the synthetic polymer film 34A shown in FIG. 1(a) but also surficial nanostructures that are formed by raised portions which have a part where the cross-sectional area a cross section parallel to the film surface) is constant as do the raised portions 34Bp of the synthetic polymer film 34B shown in FIG. 1(b). Note that, from the viewpoint of breaking the cell walls and/or cell membranes of microorganisms, providing a conical portion is preferred. Note that, however, the tip end of the conical shape does not necessarily need to be a surficial nanostructure but may have a rounded portion (about 60 nm) which is generally equal to the nanopillars which form surficial nanostructures of the wings of cicadas.

A mold for forming the moth-eye structure such as illustrated in FIGS. 1(a) and 1(b) over the surface (hereinafter, referred to as "moth-eye mold") has an inverted moth-eye structure obtained by inverting the moth-eye structure. Using an anodized porous alumina layer which has the inverted moth-eye structure as a mold without any modification enables inexpensive production of the moth-eye structure. Particularly when a moth-eye mold in the shape of a hollow cylinder is used, the moth-eye structure can be efficiently manufactured according to a roll-to-roll method. Such a moth-eye mold can be manufactured according to methods disclosed in Patent Documents 2 to 4.

A manufacturing method of a moth-eye mold 100A that is for production of the synthetic polymer film 34A is described with reference to FIGS. 2(a) to 2(e).

Firstly, a mold base 10 is provided which includes an aluminum base 12, an inorganic material layer 16 provided on a surface of the aluminum base 12, and an aluminum film 18 deposited on the inorganic material layer 16 as shown in FIG. 2(a).

The aluminum base 12 used may be an aluminum base whose aluminum purity is not less than 99.50 mass % and less than 99.99 mass % and which has relatively high rigidity. The impurity contained in the aluminum base 12 may preferably include at least one element selected from the group consisting of iron (Fe), silicon (Si), copper (Cu), manganese (Mn), zinc (Zn), nickel (Ni), titanium (Ti), lead (Pb), tin (Sn) and magnesium (Mg). Particularly, Mg is preferred. Since the mechanism of formation of pits (hollows) in the etching step is a local cell reaction, the aluminum base 12 ideally does not contain any element which is nobler than aluminum. It is preferred that the aluminum base 12 used contains, as the impurity element, Mg (standard electrode potential: −2.36 V) which is a base metal. If the content of an element nobler than aluminum is 10 ppm or less, it can be said in terms of electrochemistry that the aluminum base 12 does not substantially contain the element. The Mg content is preferably 0.1 mass % or more of the whole. It is, more preferably, in the range of not more than about 3.0 mass %. If the Mg content is less than 0.1 mass %, sufficient rigidity cannot be obtained. On the other hand, as the Mg content increases, segregation of Mg is more likely to occur. Even if the segregation occurs near a surface over which a moth-eye mold is to be formed, it would not be detrimental in terms of electrochemistry but would be a cause of a defect because Mg forms an anodized film of a different form from that of aluminum. The content of the impurity element may be appropriately determined depending on the shape, thickness, and size of the aluminum base 12, in view of required rigidity. For example, when the aluminum base 12 in the form of a plate is prepared by rolling, the appropriate Mg content is about 3.0 mass %. When the aluminum base 12 having a three-dimensional structure of, for example, a hollow cylinder is prepared by extrusion, the Mg content is preferably 2.0 mass % or less. If the Mg content exceeds 2.0 mass %, the extrudability deteriorates in general.

The aluminum base 12 used may be an aluminum pipe in the shape of a hollow cylinder which is made of, for example, JIS A1050, an Al—Mg based alloy (e.g., JIS A5052), or an Al—Mg—Si based alloy (e.g., JIS A6063).

The surface of the aluminum base 12 is preferably a surface cut with a bit. If, for example, abrasive particles are remaining on the surface of the aluminum base 12, conduction will readily occur between the aluminum film 18 and the aluminum base 12 in a portion in which the abrasive particles are present. Not only in the portion in which the abrasive particles are remaining but also in a portion which has a roughened surface, conduction readily occurs between the aluminum film 18 and the aluminum base 12. When conduction occurs locally between the aluminum film 18 and the aluminum base 12, there is a probability that a local cell reaction will occur between an impurity in the aluminum base 12 and the aluminum film 18.

The material of the inorganic material layer 16 may be, for example, tantalum oxide ($Ta_2O_5$) or silicon dioxide ($SiO_2$). The inorganic material layer 16 can be formed by, for example, sputtering. When a tantalum oxide layer is used as the inorganic material layer 16, the thickness of the tantalum oxide layer is, for example, 200 nm.

The thickness of the inorganic material layer 16 is preferably not less than 100 nm and less than 500 nm. If the thickness of the inorganic material layer 16 is less than 100 nm, there is a probability that a defect (typically, a void; i.e., a gap between crystal grains) occurs in the aluminum film 18. If the thickness of the inorganic material layer 16 is not less than 500 nm, insulation is likely to occur between the aluminum base 12 and the aluminum film 18 due to the surface condition of the aluminum base 12. To realize anodization of the aluminum film 18 by supplying an electric current from the aluminum base 12 side to the aluminum film 18, the electric current needs to flow between the aluminum base 12 and the aluminum film 18. When employing a configuration where an electric current is supplied from the inside surface of the aluminum base 12 in the shape of a hollow cylinder, it is not necessary to provide an electrode to the aluminum film 18. Therefore, the aluminum film 18 can be anodized across the entire surface, while such a problem does not occur that supply of the electric current becomes more difficult as the anodization advances. Thus, the aluminum film 18 can be anodized uniformly across the entire surface.

To form a thick inorganic material layer 16, it is in general necessary to increase the film formation duration. When the film formation duration is increased, the surface temperature of the aluminum base 12 unnecessarily increases, and as a result, the film quality of the aluminum film 18 deteriorates, and a defect (typically, a void) occurs in some cases. When the thickness of the inorganic material layer 16 is less than 500 nm, occurrence of such a problem can be suppressed.

The aluminum film 18 is, for example, a film which is made of aluminum whose purity is not less than 99.99 mass % (hereinafter, sometimes referred to as "high-purity aluminum film") as disclosed in Patent Document 3. The aluminum film is formed by, for example, vacuum evaporation or sputtering. The thickness of the aluminum film 18 is preferably in the range of not less than about 500 nm and not more than about 1500 nm. For example, the thickness of the aluminum film 18 is about 1 µm.

The aluminum film 18 may be an aluminum alloy film disclosed in Patent Document 4 in substitution for the high-purity aluminum film. The aluminum alloy film disclosed in Patent Document 4 contains aluminum, a metal element other than aluminum, and nitrogen. In this specification, the "aluminum film" includes not only the high-purity aluminum film but also the aluminum alloy film disclosed in Patent Document 4.

Using the above-described aluminum alloy film enables to obtain a specular surface whose reflectance is not less than 80%. The average grain diameter of crystal grains that form the aluminum alloy film when viewed in the normal direction of the aluminum alloy film is, for example, not more than 100 nm, and that the maximum surface roughness Rmax of the aluminum alloy film is not more than 60 nm. The content of nitrogen in the aluminum alloy film is, for example, not less than 0.5 mass % and not more than 5.7 mass %. It is preferred that the absolute value of the difference between the standard electrode potential of the metal element other than aluminum which is contained in the aluminum alloy film and the standard electrode potential of aluminum is not more than 0.64 V, and that the content of the metal element in the aluminum alloy film is not less than 1.0 mass % and not more than 1.9 mass %. The metal element is, for example, Ti or Nd. The metal element is not limited to these examples but may be such a different metal element that the absolute value of the difference between the standard electrode potential of the metal element and the standard electrode potential of aluminum is not more than 0.64 V (for example, Mn, Mg, Zr, V, and Pb). Further, the metal element may be Mo, Nb, or Hf. The aluminum alloy film may contain two or more of these metal elements. The aluminum alloy film is formed by, for example, a DC magnetron sputtering method. The thickness of the aluminum alloy film is also preferably in the range of not less than about 500 nm and not more than about 1500 nm. For example, the thickness of the aluminum alloy film is about 1 μm.

Then, a surface 18s of the aluminum film 18 is anodized to form a porous alumina layer 14 which has a plurality of recessed portions (micropores) 14p as shown in FIG. 2(b). The porous alumina layer 14 includes a porous layer which has the recessed portions 14p and a barrier layer (the base of the recessed portions (micropores) 14p). As known in the art, the interval between adjacent recessed portions 14p (the distance between the centers) is approximately twice the thickness of the barrier layer and is approximately proportional to the voltage that is applied during the anodization. This relationship also applies to the final porous alumina layer 14 shown in FIG. 2(e).

The porous alumina layer 14 is formed by, for example, anodizing the surface 18s in an acidic electrolytic solution. The electrolytic solution used in the step of forming the porous alumina layer 14 is, for example, an aqueous solution which contains an acid selected from the group consisting of oxalic acid, tartaric acid, phosphoric acid, sulfuric acid, chromic acid, citric acid, and malic acid. For example, the surface 18s of the aluminum film 18 is anodized with an applied voltage of 80 V for 55 seconds using an oxalic acid aqueous solution (concentration: 0.3 mass %, solution temperature: 10° C.), whereby the porous alumina layer 14 is formed.

Then, the porous alumina layer 14 is brought into contact with an alumina etchant such that a predetermined amount is etched away, whereby the opening of the recessed portions 14p is enlarged as shown in FIG. 2(c). By modifying the type and concentration of the etching solution and the etching duration, the etching amount (i.e., the size and depth of the recessed portions 14p) can be controlled. The etching solution used may be, for example, an aqueous solution of 10 mass % phosphoric acid, organic acid such as formic acid, acetic acid or citric acid, or sulfuric acid, or a chromic/phosphoric acid solution. For example, the etching is performed for 20 minutes using a phosphoric acid aqueous solution (10 mass %, 30° C.)

Then, the aluminum film 18 is again partially anodized such that the recessed portions 14p are grown in the depth direction and the thickness of the porous alumina layer 14 is increased as shown in FIG. 2(d). Here, the growth of the recessed portions 14p starts at the bottoms of the previously-formed recessed portions 14p, and accordingly, the lateral surfaces of the recessed portions 14p have stepped shapes.

Thereafter, when necessary, the porous alumina layer 14 may be brought into contact with an alumina etchant to be further etched such that the pore diameter of the recessed portions 14p is further increased. The etching solution used in this step may preferably be the above-described etching solution. Practically, the same etching bath may be used.

In this way, by alternately repeating the anodization step and the etching step as described above through multiple cycles (e.g., 5 cycles: including 5 anodization cycles and 4 etching cycles), the moth-eye mold 100A that includes the porous alumina layer 14 which has the inverted moth-eye structure is obtained as shown in FIG. 2(e). Since the process is ended with the anodization step, the recessed portions 14p have pointed bottom portion. That is, the resultant mold enables formation of raised portions with pointed tip ends.

The porous alumina layer 14 (thickness: $t_p$) shown in FIG. 2(e) includes a porous layer (whose thickness is equivalent to the depth $D_d$ of the recessed portions 14p) and a barrier layer (thickness: $t_b$). Since the porous alumina layer 14 has a structure obtained by inverting the moth-eye structure of the synthetic polymer film 34A, corresponding parameters which define the dimensions may sometimes be designated by the same symbols.

The recessed portions 14p of the porous alumina layer 14 may have, for example, a conical shape and may have a stepped lateral surface. It is preferred that the two-dimensional size of the recessed portions 14p (the diameter of a circle equivalent to the area of the recessed portions 14p when viewed in a normal direction of the surface), $D_p$, is more than 20 nm and less than 500 nm, and the depth of the recessed portions 14p, $D_d$, is not less than 50 nm and less than 1000 nm (1 μm). It is also preferred that the bottom portion of the recessed portions 14p is acute (with the deepest part of the bottom portion being pointed). When the recessed portions 14p are in a densely packed arrangement, assuming that the shape of the recessed portions 14p when viewed in a normal direction of the porous alumina layer 14 is a circle, adjacent circles overlap each other, and a saddle portion is formed between adjacent ones of the recessed portions 14p. Note that, when the generally-conical recessed portions 14p adjoin one another so as to form saddle portions, the two-dimensional size of the recessed portions 14p, $D_p$, is equal to the adjoining distance $D_{int}$. The thickness of the porous alumina layer 14, $t_p$, is not more than about 1 μm.

Under the porous alumina layer 14 shown in FIG. 2(e), there is an aluminum remnant layer 18r. The aluminum remnant layer 18r is part of the aluminum film 18 which has not been anodized. When necessary, the aluminum film 18 may be substantially thoroughly anodized such that the aluminum remnant layer 18r is not present. For example, when the inorganic material layer 16 has a small thickness, it is possible to readily supply an electric current from the aluminum base 12 side.

The manufacturing method of the moth-eye mold illustrated herein enables manufacture of a mold which is for production of antireflection films disclosed in Patent Documents 2 to 4. Since an antireflection film used in a high-definition display panel is required to have high uniformity, selection of the material of the aluminum base, specular working of the aluminum base, and control of the purity and components of the aluminum film are preferably carried out as described above. However, the above-described mold manufacturing method can be simplified because the microbicidal activity can be achieved without high uniformity. For example, the surface of the aluminum base may be directly anodized. Even if, in this case, pits are formed due to impurities contained in the aluminum base, only local structural irregularities occur in the moth-eye structure of the finally-obtained synthetic polymer film 34A, and it is estimated that there is little adverse influence on the microbicidal activity.

According to the above-described mold manufacturing method, a mold in which the regularity of the arrangement of the recessed portions is low, and which is suitable to production of an antireflection film, can be manufactured. In the case of utilizing the microbicidal ability of the moth-eye structure, it is estimated that the regularity of the arrangement of the raised portions does not exert an influence. A mold for formation of a moth-eye structure which has regularly-arranged raised portions can be manufactured, for example, as described in the following section.

For example, after formation of a porous alumina layer having a thickness of about 10 μm, the formed porous alumina layer is removed by etching, and then, anodization may be performed under the conditions for formation of the above-described porous alumina layer. A 10 μm thick porous alumina layer is realized by extending the anodization duration. When such a relatively thick porous alumina layer is formed and then this porous alumina layer is removed, a porous alumina layer having regularly-arranged recessed portions can be formed without being influenced by irregularities which are attributed to grains that are present at the surface of an aluminum film or aluminum base or the process strain. Note that, in removal of the porous alumina layer, using a chromic/phosphoric acid solution is preferred. Although continuing the etching for a long period of time sometimes causes galvanic corrosion, the chromic/phosphoric acid solution has the effect of suppressing galvanic corrosion.

A moth-eye mold for production of the synthetic polymer film 34B shown in FIG. 1(b) can be, basically, manufactured by combination of the above-described anodization step and etching step. A manufacturing method of a moth-eye mold 100B that is for production of the synthetic polymer film 34B is described with reference to FIGS. 3(a) to 3(c).

Firstly, in the same way as illustrated with reference to FIGS. 2(a) and 2(b), the mold base 10 is provided, and the surface 18s of the aluminum film 18 is anodized, whereby a porous alumina layer 14 which has a plurality of recessed portions (micropores) 14p is formed.

Figure 2:
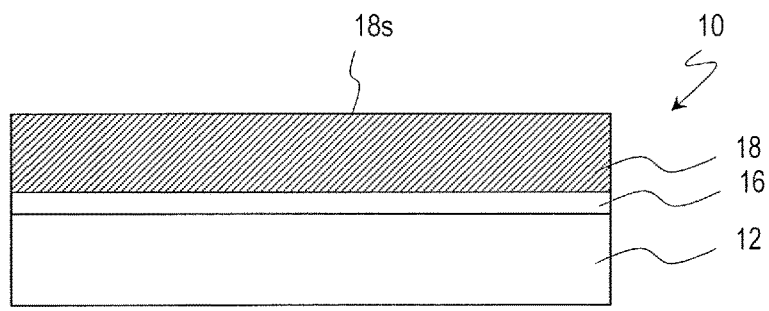
FIGS. 2(a) to 2(e) are diagrams for illustrating a method for manufacturing a moth-eye mold 100A and a configuration of the moth-eye mold 100A.
Figure 2:
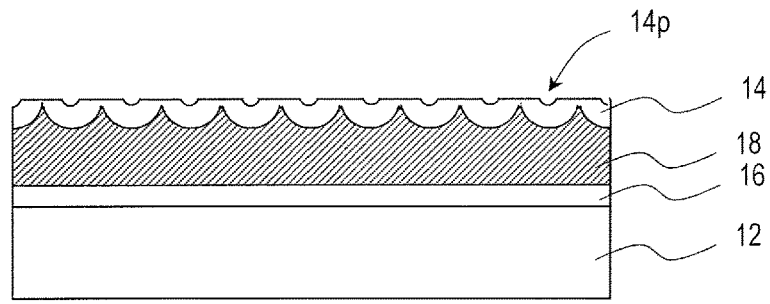
Figure 2:
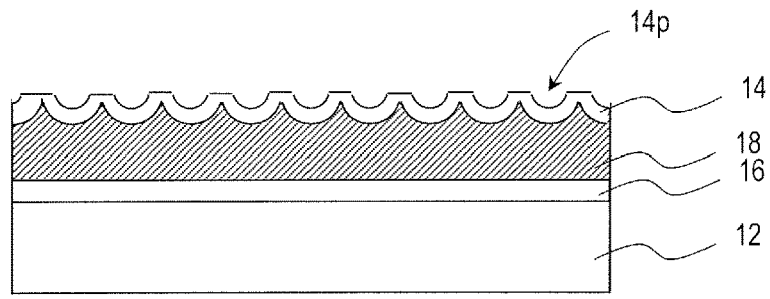
Figure 2:
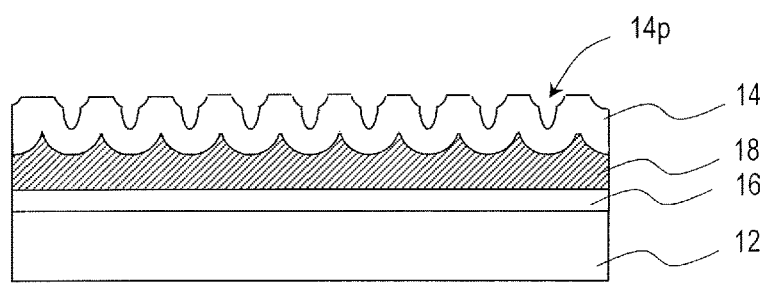
Figure 2:
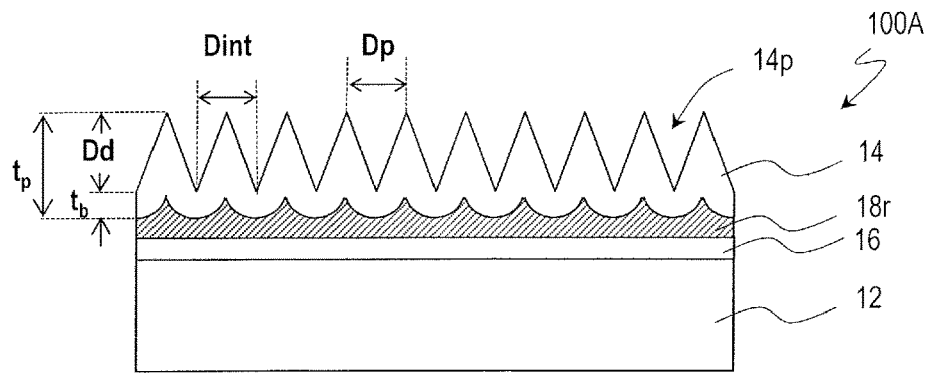
Figure 3:
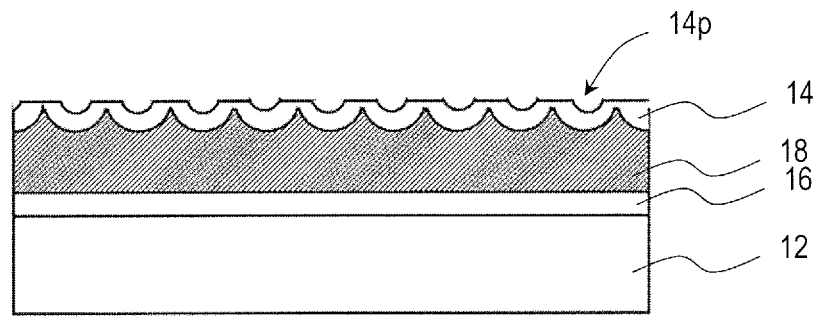
FIGS. 3(a) to 3(c) are diagrams for illustrating a method for manufacturing a moth-eye mold 100B and a configuration of the moth-eye mold 100B.
Figure 3:
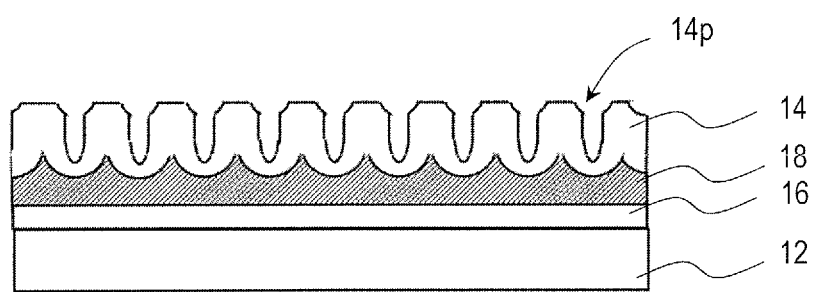
Figure 3:
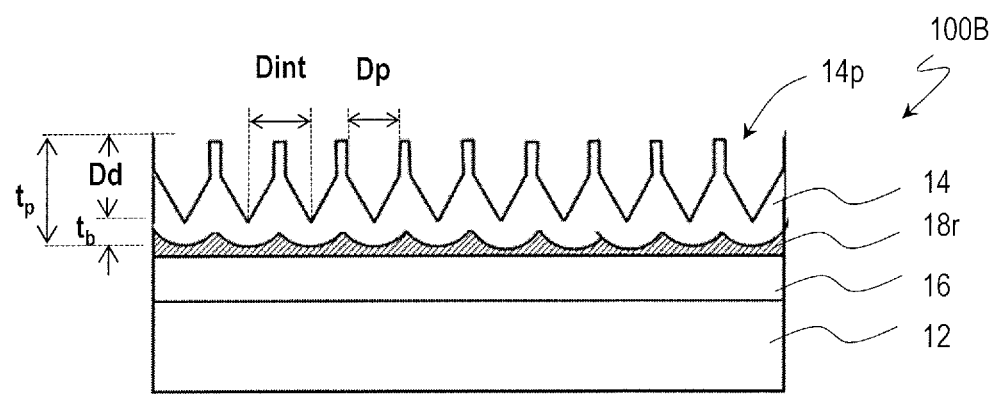

Then, the porous alumina layer 14 is brought into contact with an alumina etchant such that a predetermined amount is etched away, whereby the opening of the recessed portions 14p is enlarged as shown in FIG. 3(a). In this step, the etched amount is smaller than in the etching step illustrated with reference to FIG. 2(c). That is, the size of the opening of the recessed portions 14p is decreased. For example, the etching is performed for 10 minutes using a phosphoric acid aqueous solution (10 mass %, 30° C.)

Then, the aluminum film 18 is again partially anodized such that the recessed portions 14p are grown in the depth direction and the thickness of the porous alumina layer 14 is increased as shown in FIG. 3(b). In this step, the recessed portions 14p are grown deeper than in the anodization step illustrated with reference to FIG. 2(d). For example, the anodization is carried out with an applied voltage of 80 V for 165 seconds (in FIG. 2(d), 55 seconds) using an oxalic acid aqueous solution (concentration: 0.3 mass %, solution temperature: 10° C.)

Thereafter, the etching step and the anodization step are alternately repeated through multiple cycles in the same way as illustrated with reference to FIG. 2(e). For example, 3 cycles of the etching step and 3 cycles of the anodization step are alternately repeated, whereby the moth-eye mold 100B including the porous alumina layer 14 which has the inverted moth-eye structure is obtained as shown in FIG. 3(c). In this step, the two-dimensional size of the recessed portions 14p, $D_p$, is smaller than the adjoining distance $D_{int}$ ($D_p < D_{int}$).

The size of the microorganisms varies depending on their types. For example, the size of P. aeruginosa is about 1 μm. However, the size of the bacteria ranges from several hundreds of nanometers to about five micrometers. The size of fungi is not less than several micrometers. It is estimated that, for example, raised portions whose two-dimensional size is about 200 nm have a microbicidal activity on a microorganism whose size is not less than about 0.5 μm, but there is a probability that the raised portions are too large to exhibit a sufficient microbicidal activity on a bacterium whose size is several hundreds of nanometers. The size of viruses ranges from several tens of nanometers to several hundreds of nanometers, and many of them have a size of not more than 100 nm. Note that viruses do not have a cell membrane but have a protein shell called capsid which encloses virus nucleic acids. The viruses can be classified into those which have a membrane-like envelope outside the shell and those which do not have such an envelope. In the viruses which have an envelope, the envelope is mainly made of a lipid. Therefore, it is expected that the raised portions likewise act on the envelope. Examples of the viruses which have an envelope include influenza virus and Ebola virus. In the viruses which do not have an envelope, it is expected that the raised portions likewise act on this protein shell called capsid. When the raised portions include nitrogen element, the raised portions can have an increased affinity for a protein which is made of amino acids.

In view of the above, the configuration and production method of a synthetic polymer film having raised portions which can exhibit a microbicidal activity against a microorganism of not more than several hundreds of nanometers are described below.

In the following description, raised portions of the above-described synthetic polymer film which have a two-dimensional size in the range of more than 20 nm and less than 500 nm are referred to as "first raised portions". Raised portions which are superimposedly formed over the first raised portions are referred to as "second raised portions". The two-dimensional size of the second raised portions is smaller than the two-dimensional size of the first raised portions and does not exceed 100 nm. Note that when the two-dimensional size of the first raised portions is less than 100 nm, particularly less than 50 nm, it is not necessary to provide the second raised portions. Recessed portions of the mold corresponding to the first raised portions are referred to as "first recessed portions", and recessed portions of the mold corresponding to the second raised portions are referred to as "second recessed portions".

When the method of forming the first recessed portions which have predetermined size and shape by alternately performing the anodization step and the etching step as described above is applied without any modification, the second recessed portions cannot be formed successfully.

Figure 4:
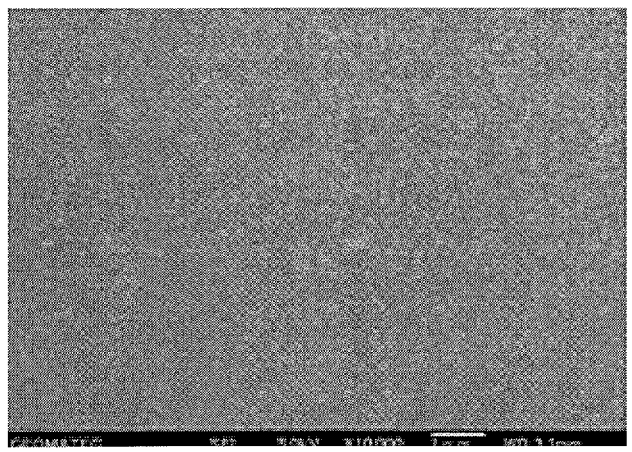
FIG. 4(a) shows a SEM image of a surface of an aluminum base.
FIG. 4(b) shows a SEM image of a surface of an aluminum film.
FIG. 4(c) shows a SEM image of a cross section of the aluminum film.
Figure 4:
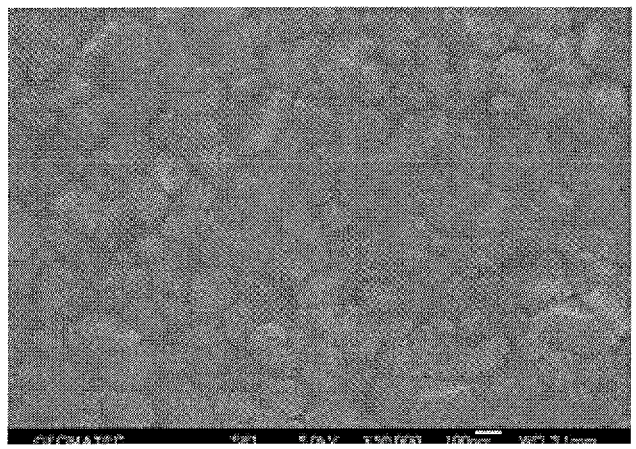
Figure 4:
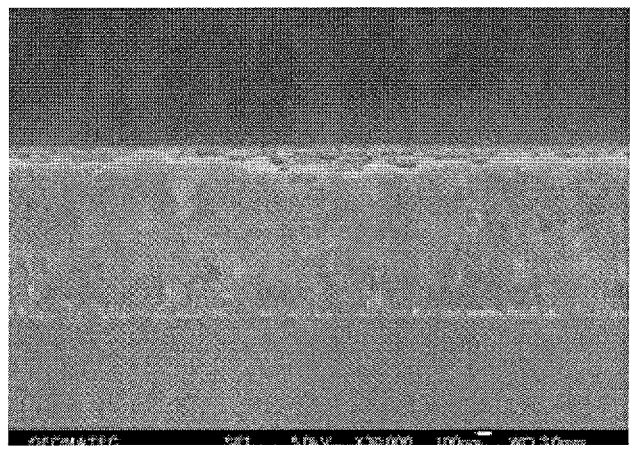

FIG. 4(a) shows a SEM image of a surface of an aluminum base (designated by reference numeral 12 in FIG. 2). FIG. 4(b) shows a SEM image of a surface of an aluminum film (designated by reference numeral 18 in FIG. 2). FIG. 4(c) shows a SEM image of a cross section of the aluminum film (designated by reference numeral 18 in FIG. 2). As seen from these SEM images, there are grains (crystal grains) at the surface of the aluminum base and the surface of the aluminum film. The grains of the aluminum film form unevenness at the surface of the aluminum film. This unevenness at the surface affects formation of the recessed portions in the anodization and therefore interrupts formation of second recessed portions whose $D_p$ or $D_{int}$ is smaller than 100 nm.

In view of the above, a mold manufacturing method according to an embodiment of the present invention includes: (a) providing an aluminum base or an aluminum film deposited on a support; (b) the anodization step of applying a voltage at the first level while a surface of the aluminum base or aluminum film is kept in contact with an electrolytic solution, thereby forming a porous alumina layer which has the first recessed portions; (c) after step (b), the etching step of bringing the porous alumina layer into contact with an etching solution, thereby enlarging the first recessed portions; and (d) after step (c), applying a voltage at the second level that is lower than the first level while the porous alumina layer is kept in contact with an electrolytic solution, thereby forming the second recessed portions in the first recessed portions. For example, the first level is higher than 40 V, and the second level is equal to or lower than 20 V.

Specifically, an anodization step is carried out with the voltage at the first level, whereby the first recessed portions are formed which have such a size that is not influenced by the grains of the aluminum base or aluminum film. Thereafter, the thickness of the barrier layer is decreased by etching, and then, another anodization step is carried out with the voltage at the second level that is lower than the first level, whereby the second recessed portions are formed in the first recessed portions. When the second recessed portions are formed through such a procedure, the influence of the grains is avoided.

Figure 5:
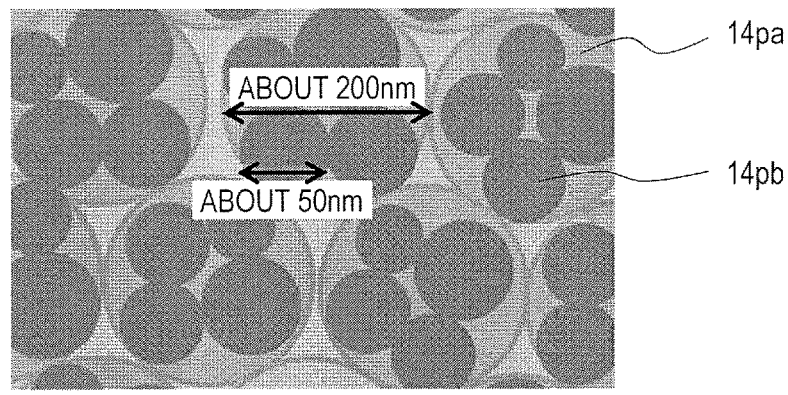
FIG. 5(a) is a schematic plan view of a porous alumina layer of a mold.
FIG. 5(b) is a schematic cross-sectional view of the porous alumina layer.
FIG. 5(c) is a SEM image of a prototype mold.
Figure 5:
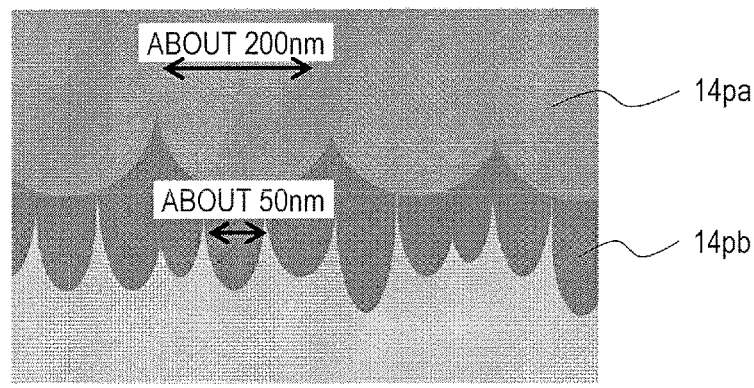
Figure 5:
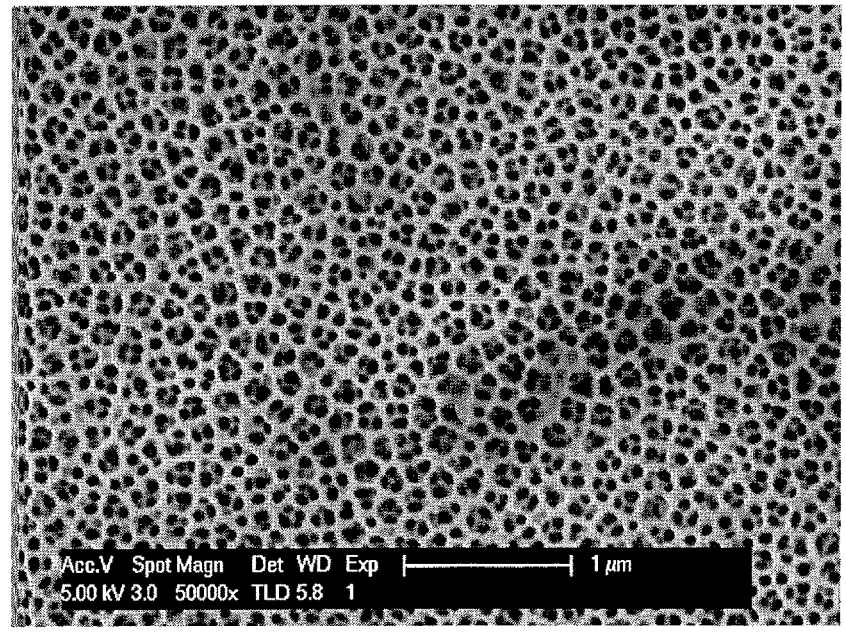

A mold which has first recessed portions 14*pa* and second recessed portions 14*pb* formed in the first recessed portions 14*pa* is described with reference to FIG. 5. FIG. 5(*a*) is a schematic plan view of a porous alumina layer of a mold. FIG. 5(*b*) is a schematic cross-sectional view of the porous alumina layer. FIG. 5(*c*) shows a SEM image of a prototype mold.

As shown in FIGS. 5(*a*) and 5(*b*), the surface of the mold of the present embodiment has the plurality of first recessed portions 14*pa* whose two-dimensional size is in the range of more than 20 nm and less than 500 nm and the plurality of second recessed portions 14*pb* which are superimposedly formed over the plurality of first recessed portions 14*pa*. The two-dimensional size of the plurality of second recessed portions 14*pb* is smaller than the two-dimensional size of the plurality of first recessed portions 14*pa* and does not exceed 100 nm. The height of the second recessed portions 14*pb* is, for example, more than 20 nm and not more than 100 nm. The second recessed portions 14*pb* preferably have a generally conical portion as do the first recessed portions 14*pa*.

The porous alumina layer shown in FIG. 5(*c*) was formed as described below.

The aluminum film used was an aluminum film which contains Ti at 1 mass %. The anodization solution used was an oxalic acid aqueous solution (concentration: 0.3 mass %, solution temperature: 10° C.). The etching solution used was a phosphoric acid aqueous solution (concentration: 10 mass %, solution temperature: 30° C.). After the anodization was carried out with a voltage of 80 V for 52 seconds, the etching was carried out for 25 minutes. Then, the anodization was carried out with a voltage of 80 V for 52 seconds, and the etching was carried out for 25 minutes. Thereafter, the anodization was carried out with a voltage of 20 V for 52 seconds, and the etching was carried out for 5 minutes. Further, the anodization was carried out with a voltage of 20 V for 52 seconds.

As seen from FIG. 5(*c*), the second recessed portions whose $D_p$ was about 50 nm were formed in the first recessed portions whose $D_p$ was about 200 nm. When in the above-described manufacturing method the voltage at the first level was changed from 80 V to 45 V for formation of the porous alumina layer, the second recessed portions whose $D_p$ was about 50 nm were formed in the first recessed portions whose $D_p$ was about 100 nm.

When a synthetic polymer film is produced using such a mold, the produced synthetic polymer film has raised portions whose configuration is the inverse of that of the first recessed portions 14*pa* and the second recessed portions 14*pb* shown in FIGS. 5(*a*) and 5(*b*). That is, the produced synthetic polymer film further includes a plurality of second raised portions superimposedly formed over a plurality of first raised portions.

The thus-produced synthetic polymer film which has the first raised portions and the second raised portions superimposedly formed over the first raised portions has a microbicidal activity on various microorganisms, ranging from relatively small microorganisms of about 100 nm to relatively large microorganisms of not less than 5 μm.

As a matter of course, only raised portions whose two-dimensional size is in the range of more than 20 nm and less than 100 nm may be formed according to the size of a target microorganism. The mold for formation of such raised portions can be manufactured, for example, as described below.

The anodization is carried out using a neutral salt aqueous solution (ammonium borate, ammonium citrate, etc.), such as an ammonium tartrate aqueous solution, or an organic acid which has a low ionic dissociation degree (maleic acid, malonic acid, phthalic acid, citric acid, tartaric acid, etc.) to form a barrier type anodized film. After the barrier type anodized film is removed by etching, the anodization is carried out with a predetermined voltage (the voltage at the second level described above), whereby recessed portions whose two-dimensional size is in the range of more than 20 nm and less than 100 nm can be formed.

For example, an aluminum film which contains Ti at 1 mass % is anodized at 100 V for 2 minutes using a tartaric acid aqueous solution (concentration: 0.1 mol/l, solution temperature: 23° C.), whereby a barrier type anodized film is formed. Thereafter, the etching is carried out for 25 minutes using a phosphoric acid aqueous solution (concentration: 10 mass %, solution temperature: 30° C.), whereby the barrier type anodized film is removed. Thereafter, the anodization and the etching are alternatively repeated as described above, specifically through 5 anodization cycles and 4 etching cycles. The anodization was carried out at 20 V for 52 seconds using an oxalic acid aqueous solution (concentration: 0.3 mass %, solution temperature: 10° C.) as the anodization solution. The etching Was carried out for 5 minutes using the above-described etching solution. As a result, recessed portions whose two-dimensional size is about 50 nm can be uniformly formed.

Moth-eye molds which are capable of forming various moth-eye structures can be manufactured as described above.

Figure 6:
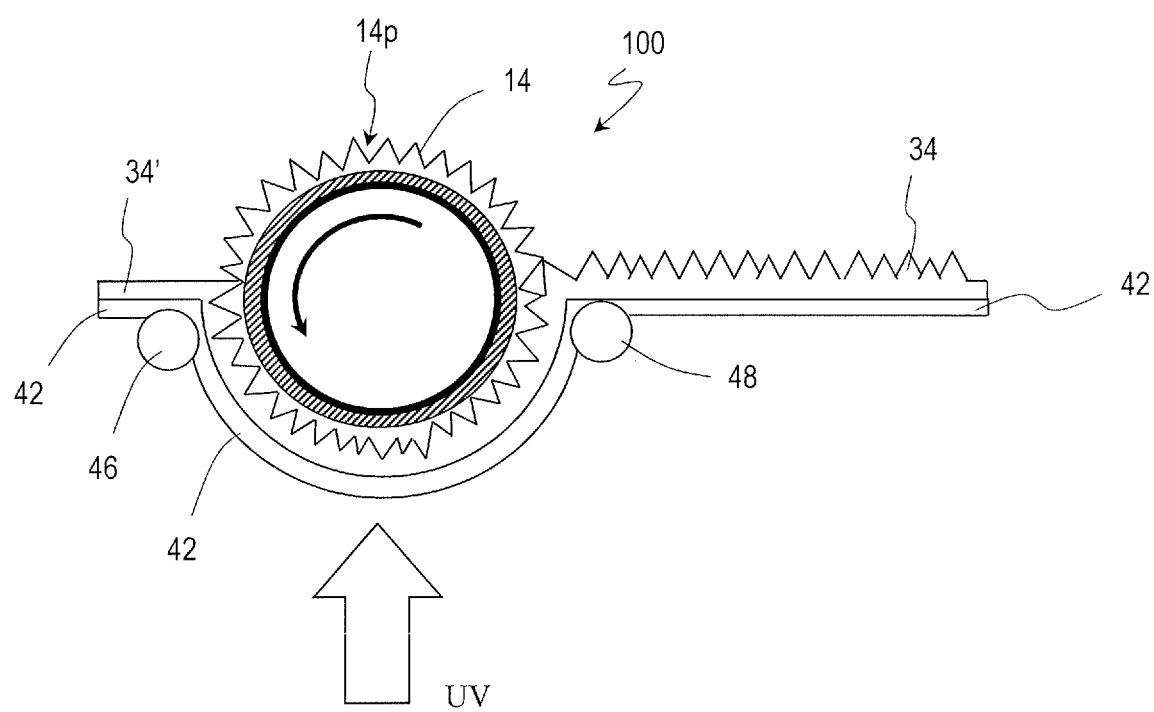
FIG. 6 is a diagram for illustrating a method for producing a synthetic polymer film with the use of the moth-eye mold 100.

Next, a method for producing a synthetic polymer film with the use of a moth-eye mold 100 is described with reference to FIG. 6. FIG. 6 is a schematic cross-sectional view for illustrating a method for producing a synthetic polymer film according to a roll-to-roll method.

First, a moth-eye mold 100 in the shape of a hollow cylinder is provided. Note that the moth-eye mold 100 in the shape of a hollow cylinder is manufactured according to, for example, the manufacturing method described with reference to FIG. 2.

As shown in FIG. 6, a base film 42 over which a UV-curable resin 34' is applied on its surface is maintained pressed against the moth-eye mold 100, and the UV-curable resin 34' is irradiated with ultraviolet (UV) light such that the UV-curable resin 34' is cured. The UV-curable resin 34' used may be, for example, an acrylic resin. The base film 42 may be, for example, a PET (polyethylene terephthalate) film or TAG (triacetyl cellulose) film. The base film 42 is fed from an unshown feeder roller, and thereafter, the UV-curable resin 34' is applied over the surface of the base film 42 using, for example, a slit coater or the like. The base film 42 is supported by supporting rollers 46 and 48 as shown in FIG. 6. The supporting rollers 46 and 48 have rotation mechanisms for carrying the base film 42. The moth-eye mold 100 in the shape of a hollow cylinder is rotated at a rotation speed corresponding to the carrying speed of the base film 42 in a direction indicated by the arrow in FIG. 6.

Thereafter, the moth-eye mold 100 is separated from the base film 42, whereby a synthetic polymer film 34 to which the inverted moth-eye structure of the moth-eye mold 100 is transferred is formed on the surface of the base film 42. The base film 42 which has the synthetic polymer film 34 formed on the surface is wound up by an unshown winding roller.

The surface of the synthetic polymer film 34 has the moth-eye structure obtained by inverting the surficial nanostructures of the moth-eye mold 100. According to the surficial nanostructure of the moth-eye mold 100 used, the synthetic polymer films 34A and 34B shown in FIGS. 1(*a*) and 1(*b*), respectively, can be produced. The material that forms the synthetic polymer film 34 is not limited to the UV-curable resin but may be a photocurable resin which is curable by visible light or may be a thermosetting resin.

The microbicidal ability of a synthetic polymer film which has the moth-eye structure over its surface has not only a correlation with the physical structure of the synthetic polymer film but also a correlation with the chemical properties of the synthetic polymer film. For example, the present applicant found correlations with chemical properties, such as a correlation with the contact angle of the surface of the synthetic polymer film (Patent Publication 1: Japanese Patent No. 5788128) and a correlation with the concentration of the nitrogen element contained in the surface (International Publication 2: WO 2016/080245, International Application 3: PCT/JP2016/068273). As disclosed in International Publication 2, the concentration of the nitrogen element at the surface is preferably not less than 0.7 at %. In International Application 3, it was found that a synthetic polymer film which has a still lower nitrogen element concentration can also have microbicidal ability. As disclosed in International Application 3, the nitrogen element concentration is preferably not less than 0.29 at % in order that the synthetic polymer film has an antimicrobial effect, and is preferably not less than 0.33 at % in order that the synthetic polymer film has a microbicidal effect. These nitrogen element concentration values disclosed in International Application 3 are the concentration of the total of nitrogen elements which are constituents of the primary amines and nitrogen elements which are constituents of the secondary amines, i.e., not including nitrogen elements which are constituents of the tertiary amines. In International Application 3, a correlation between the water resistance of the synthetic polymer film and the ethylene oxide group or ethylene oxide unit (hereinafter, also referred to as "EO unit") was also found. The number of moles of EO units is preferably more than 0.0020 and not more than 0.0080 in order that the synthetic polymer film has both water resistance and antimicrobial effect, and is preferably not less than 0.0040 and not more than 0.0080 in order that the synthetic polymer film has both water resistance and microbicidal effect. The entire disclosures of Patent Publication 1, International Publication 2 and International Application 3 are incorporated by reference in this specification.

Figure 7:
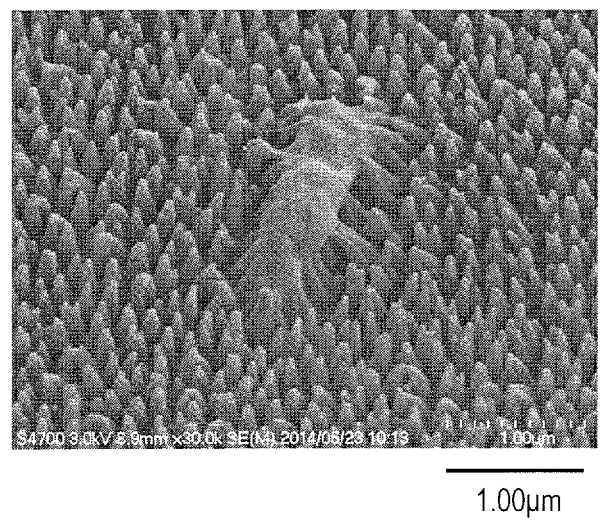
FIGS. 7(a) and 7(b) show SEM images obtained by SEM (Scanning Electron Microscope) observation of a *P. aeruginosa* bacterium which died at a surface which had a moth-eye structure.
Figure 7:
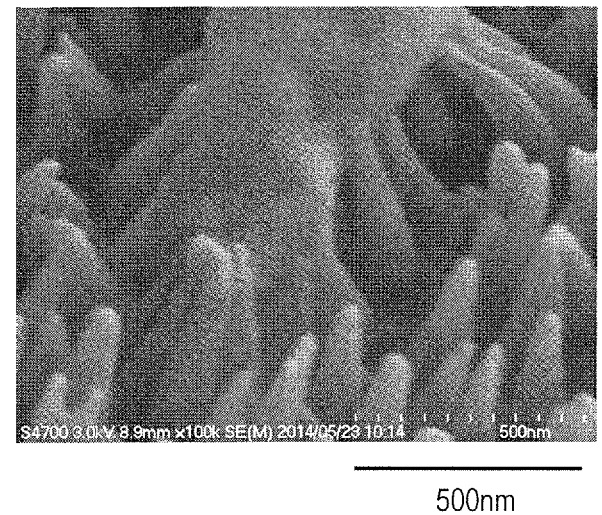
Figure 8:
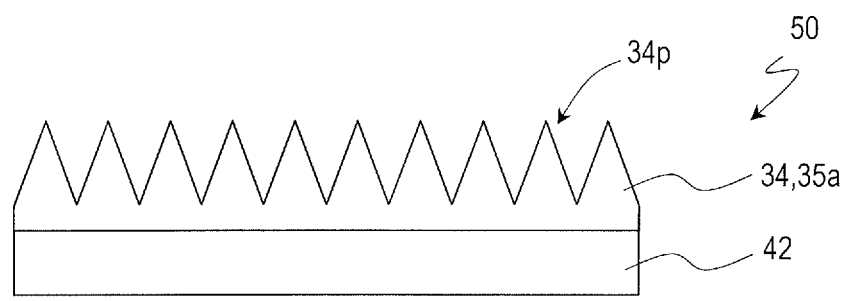
FIGS. 8(a) and 8(b) are schematic cross-sectional views for illustrating a production method and a configuration of a synthetic polymer film 35 of another embodiment of the present invention.
Figure 8:
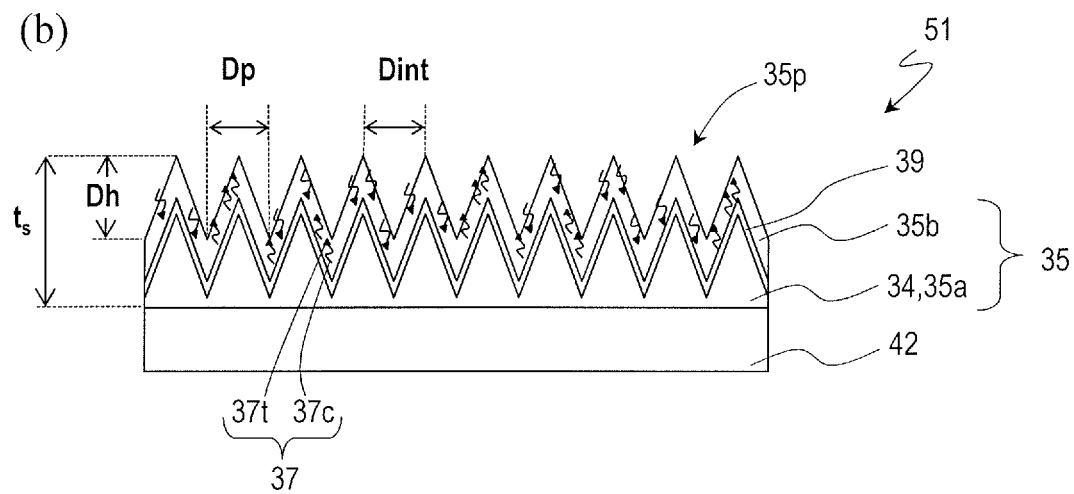

FIG. 7 shows SEM images disclosed in International Publication 2 (FIG. 8). FIGS. 7(*a*) and 7(*b*) show SEM images obtained by SEM (Scanning Electron Microscope) observation of a *P. aeruginosa* bacterium which died at the surface which had the moth-eye structure shown in FIG. 1(*a*).

As seen from these SEM images, the tip end portions of the raised portions enter the cell wall (exine) of a *P. aeruginosa* bacterium. In FIGS. 7(*a*) and 7(*b*), the raised portions do not appear to break through the cell wall but appears to be taken into the cell wall. This might be explained by the mechanism suggested in the "Supplemental Information" section of Non-patent Document 1. That is, it is estimated that the exine (lipid bilayer) of the Gram-negative bacteria came close to the raised portions and deformed so that the lipid bilayer locally underwent a transition like a first-order phase transition (spontaneous reorientation) and openings were formed in portions close to the raised portions, and the raised portions entered these openings. Alternatively, it is estimated that the raised portions were taken in due to the cell's mechanism of taking a polar substance (including a nutrient source) into the cell (endocytosis).

There is a probability that smears, such as fingerprint, adhere to the surface of the synthetic polymer film.

Antireflection films which are placed over the surface of liquid crystal television displays manufactured and sold until now by the present applicant are hydrophilic. The hydrophilicity of the moth-eye structure is for the purpose of facilitating removal of grease, such as fingerprint, adhered to the moth-eye structure with an aqueous washing solution. If the moth-eye structure is not hydrophilic, the aqueous washing solution cannot effectively enter the gap between raised portions of the moth-eye structure so that the grease cannot be removed.

However, when a fingerprint adheres to the film (synthetic polymer film) which has the hydrophilic moth-eye structure, the fingerprint (finger grease) on the film easily spreads, so that smears can become conspicuous (Problem 1). Further, grease, such as fingerprint (sebum), adhered to a hydrophilic and lipophilic synthetic polymer film cannot be sufficiently removed with a washing solution or cloth (Problem 2). When strongly wiped, there is a concern that the moth-eye structure (raised portions) might be broken and the bactericidal activity might decrease (Problem 3).

In view of such, in order to solve at least Problem 1, the present applicant carried out research on a synthetic polymer film which includes fluorine elements. A synthetic polymer film of an embodiment of the present invention includes fluorine elements and has such a profile that the fluorine content is not constant in the thickness direction and the fluorine content is higher on the raised portion side than on the side opposite to the raised portion side. The fluorine content refers to, for example, the concentration of fluorine elements. As will be described later with experimental examples, a synthetic polymer film of an embodiment of the present invention has microbicidal ability, and at the same time, grease, such as fingerprint (sebum), adhered to the synthetic polymer film is inconspicuous.

A method for producing a synthetic polymer film 35 according to an embodiment of the present invention and a configuration of the synthetic polymer film 35 are described with reference to FIG. 8. FIGS. 8(*a*) and 8(*b*) are schematic cross-sectional views for illustrating the production method of the synthetic polymer film 35 and the configuration of the synthetic polymer film 35.

As shown in FIG. 8(a), a synthetic polymer film 34 produced by the method described with reference to FIG. 6 is provided. The provided synthetic polymer film 34 is to be a lower layer resin film (or "first resin film") 35a of the synthetic polymer film 35. The synthetic polymer film 34 illustrated herein is provided on the base film 42 but is not limited to this example. The lower layer resin film 35a may not include fluorine or may include fluorine, as long as the fluorine content of the lower layer resin film 35a is lower than the fluorine content of the upper layer resin film 35b.

As shown in FIG. 8(b), an upper layer resin film (or "second resin film") 35b which includes a fluorine-containing mold releasing agent 37 is formed on the lower layer resin film 35a. When forming the upper layer resin film 35b, the lower layer resin film 35a is already cured. The upper layer resin film 35b is formed so as to cover at least some of the plurality of raised portions 34p of the synthetic polymer film 34 (lower layer resin film 35a). The upper layer resin film 35b may be formed so as to cover all of the plurality of raised portions 34p of the synthetic polymer film 34 (lower layer resin film 35a).

The fluorine-containing mold releasing agent 37 refers to a compound which would not react with a monomer, i.e., which does not directly or indirectly form a bond (covalent bond) to the skeleton of the resin. The upper layer resin film 35b that includes the fluorine-containing mold releasing agent 37 can be made of various fluorine-containing mold releasing agents commercially-available as, for example, a fluorine-containing mold releasing agent, fluoric coating agent, fluoric anti-fingerprint agent, or the like. The fluorine-containing mold releasing agent 37 includes, for example, a fluorine-containing hydrocarbon chain 37c and alkoxysilane 37t at the terminal. Since the fluorine-containing mold releasing agent 37 includes alkoxysilane 37t, the fluorine-containing mold releasing agent 37 includes silicon (Si) elements. The fluorine-containing hydrocarbon chain 37c may include an ether bond. The upper layer resin film 35b can be formed by deposition or spraying. The viscosity of the resin that forms the upper layer resin film 35b is, for example, 0.1 cP to 100 cP.

Through the above-described process, the synthetic polymer film 35 is produced. A film 51 shown in FIG. 8(b) includes a base film 42 and a synthetic polymer film 35 provided on the base film 42. The synthetic polymer film 35 has a plurality of raised portions 35p over the surface. The plurality of raised portions 35p form a moth-eye structure. The raised portions 35p of the synthetic polymer film 35 are generally equal to the raised portions 34p of the synthetic polymer film 34 (lower layer resin film 35a) in terms of two-dimensional size $D_p$, height $D_h$ and adjoining distance $D_{int}$. When viewed in the normal direction of the synthetic polymer film 35, the two-dimensional size $D_p$ of the raised portions 35p is within the range of more than 20 nm and less than 500 nm. The thickness of the upper layer resin film 35b is, for example, not more than 10 nm. The thickness of the upper layer resin film 35b refers to a thickness in the normal direction of the synthetic polymer film 35. The thickness of the synthetic polymer film 35, $t_s$, is greater than, for example, the thickness of the synthetic polymer film 34 (lower layer resin film 35a) by the thickness of the upper layer resin film 35b.

The synthetic polymer film 35 preferably further includes an oxide film 39 interposed between the lower layer resin film 35a and the upper layer resin film 35b. That is, carrying out the step of forming an oxide film (e.g., silicon dioxide film) 39 on the lower layer resin film 35a before the step of forming the upper layer resin film 35b shown in FIG. 8(b) is preferred. The oxide film 39 reacts with alkoxysilane 37t of the upper layer resin film 35b, thereby improving the adhesion between the upper layer resin film 35b and the lower layer resin film 35a. The thickness of the oxide film 39 is, for example, 10 nm. The thickness $t_s$ of the synthetic polymer film 35 that includes the oxide film 39 is, for example, greater than the thickness of the synthetic polymer film 34 (lower layer resin film 35a) by the sum of the thickness of the upper layer resin film 35b and the thickness of the oxide film 39.

The synthetic polymer film 35 includes the upper layer resin film 35b and the lower layer resin film 35a. The fluorine content of the upper layer resin film 35b is higher than the fluorine content of the lower layer resin film 35a. Since the synthetic polymer film 35 includes the upper layer resin film 35b that includes the fluorine-containing mold releasing agent 37, grease, such as fingerprint, adhered to the synthetic polymer film 35 is unlikely to spread. Therefore, even if grease, such as fingerprint, is adhered to the synthetic polymer film 35, it will be inconspicuous.

Figure 9:
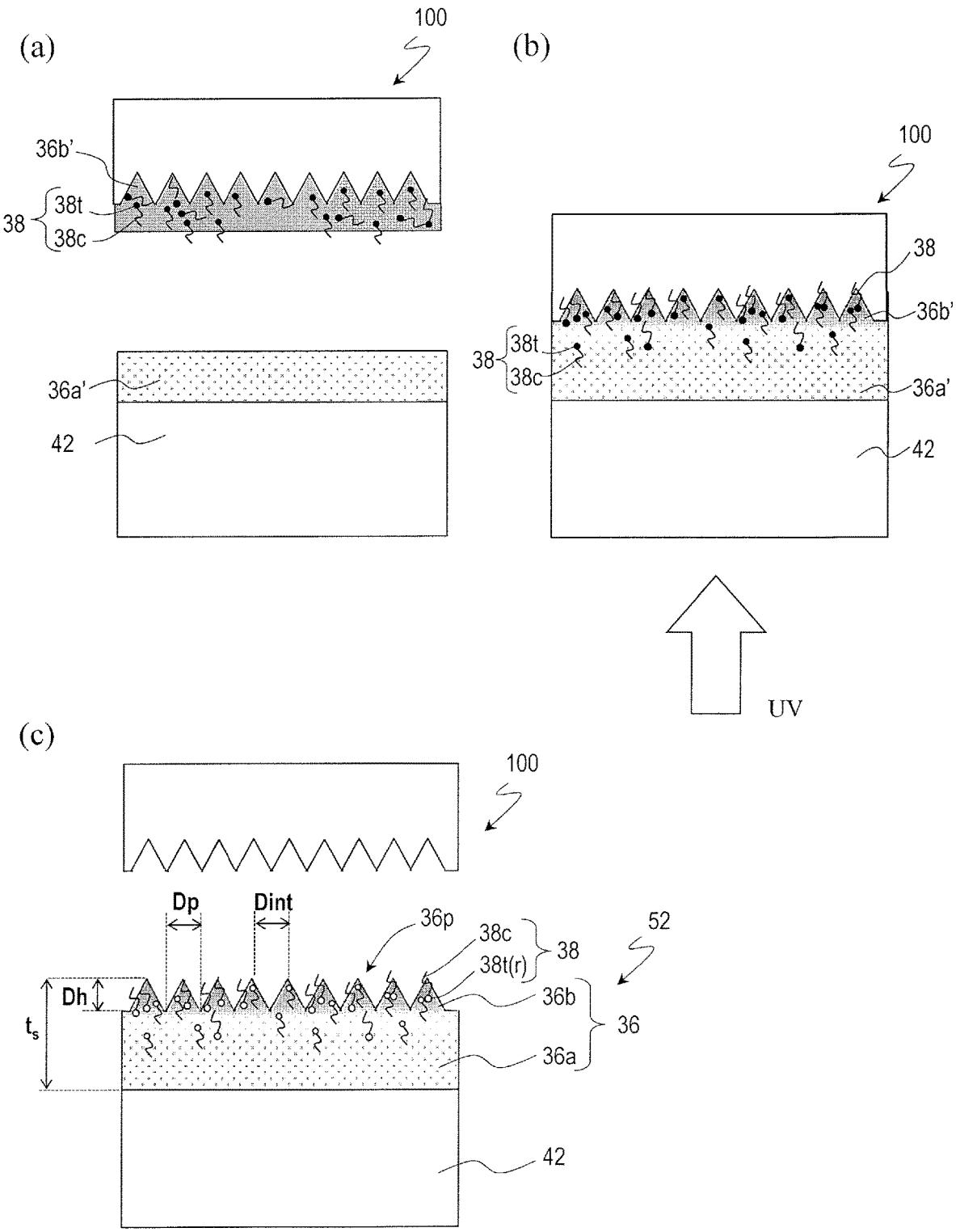
FIGS. 9(a) to 9(c) are schematic cross-sectional views for illustrating a production method and a configuration of a synthetic polymer film 36 of still another embodiment of the present invention.

The synthetic polymer film 35 is better in mass productivity than a synthetic polymer film 36 which will be described with reference to FIG. 9. The synthetic polymer film 35 can be produced using the facilities designed for production of the synthetic polymer film 34 without substantial modifications. The cost of additional facilities and machines for production of the synthetic polymer film 35 can be reduced.

As previously described with reference to FIG. 8, the production method of the synthetic polymer film 35 according to an embodiment of the present invention is a method for producing the synthetic polymer film 35 using a mold which includes a porous alumina layer, the porous alumina layer having an inverted moth-eye structure over its surface, the inverted moth-eye structure including a plurality of recessed portions whose two-dimensional size viewed in the normal direction of the surface is not less than 20 nm and less than 500 nm. The production method includes the following steps (a) to (c). Step (a) is the step of providing a mold and a work. Step (b) is the step of irradiating a first resin, which is a UV-curable resin, interposed between the mold and a surface of the work with ultraviolet light, thereby curing the first resin. Step (c) is the step of providing a second resin on the cured first resin, the second resin including a fluorine-containing mold releasing agent.

Figure 10:
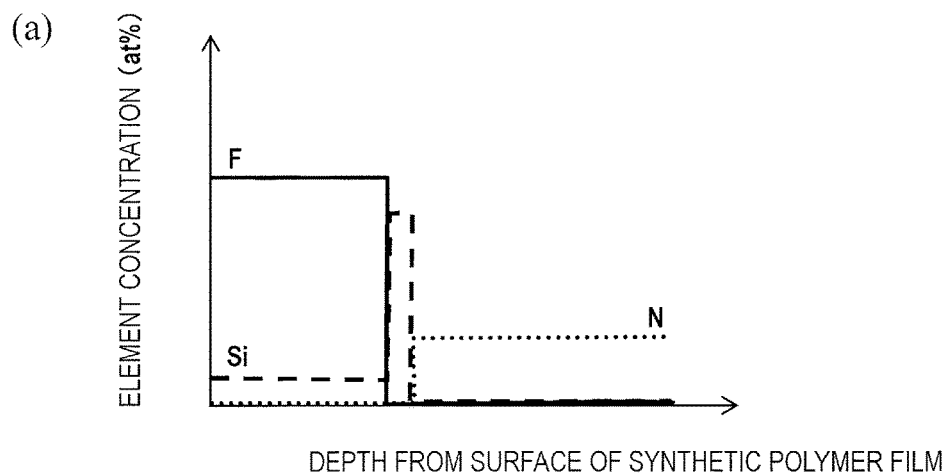
FIG. 10(a) is a graph schematically showing variations in the thickness direction of the element concentrations of fluorine (F), silicon (Si) and nitrogen (N) in the synthetic polymer film 35.
FIG. 10(b) is a graph schematically showing variations in the thickness direction of the element concentrations of fluorine (F) and nitrogen (N) in the synthetic polymer film 36.
Figure 10:
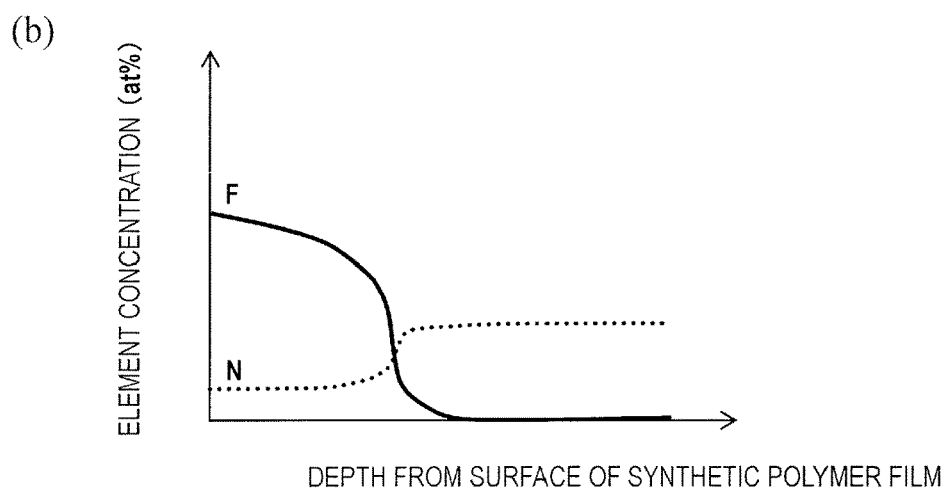

FIG. 10(a) is a graph schematically showing variations in the thickness direction (depth profiles) of the element concentrations of fluorine (F), silicon (Si) and nitrogen (N) in the synthetic polymer film 35. In FIG. 10(a), the horizontal axis represents the depth from a surface of the synthetic polymer film 35 (a surface which has the plurality of raised portions 35p), i.e., the depth in the normal direction, and the vertical axis represents the element concentration (at %) of each element. In the illustrated example, the synthetic polymer film 35 includes a silicon dioxide film 39 interposed between the upper layer resin film 35b and the lower layer resin film 35a.

As the depth from the surface of the synthetic polymer film 35 increases, the fluorine element concentration of the synthetic polymer film 35 discontinuously varies from the fluorine element concentration of the upper layer resin film 35b to the fluorine element concentration of the lower layer resin film 35a. The nitrogen element concentration of the synthetic polymer film 35 also discontinuously varies from the nitrogen element concentration of the upper layer resin film 35b to the nitrogen element concentration of the lower layer resin film 35a as the depth from the surface of the synthetic polymer film 35 increases. The silicon element concentration of the synthetic polymer film 35 also discontinuously varies from the silicon element concentration of the upper layer resin film 35b to the silicon element concentration of the lower layer resin film 35a via the silicon element concentration of the silicon dioxide film 39 as the depth from the surface of the synthetic polymer film 35 increases. The concentration of each element is generally constant in the thickness direction within each of the upper layer resin film 35b, the lower layer resin film 35a and the silicon dioxide film 39. The concentration of each element varies at the interface of the resin film and/or the oxide film.

The variation in the thickness direction of the concentration of each element in the synthetic polymer film 35 is not limited to the illustrated example. For example, although in the illustrated example the lower layer resin film 35a does not include silicon elements or fluorine elements, the element concentration in the lower layer resin film 35a can vary by arbitrarily selecting the resin material for formation of the lower layer resin film 35a. The lower layer resin film 35a may include a fluoric lubricant and/or a silicone lubricant. In the illustrated example, the upper layer resin film 35b does not include nitrogen elements.

A method for producing the synthetic polymer film 36 according to another embodiment of the present invention and a configuration of the synthetic polymer film 36 are described with reference to FIG. 9. FIGS. 9(a) to 9(c) are schematic cross-sectional views for illustrating the production method of the synthetic polymer film 36 and the configuration of the synthetic polymer film 36.

First, as shown in FIG. 9(a), a lower layer resin (or "first resin") is applied to the surface of the base film 42, whereby a lower layer resin film (or "first resin film") 36a' is formed. An upper layer resin (or "second resin") is applied to the inverted moth-eye structure of the moth-eye mold 100, whereby an upper layer resin film (or "second resin film") 36b' is formed.

The lower layer resin used can be, for example, an acrylic resin (acrylate monomer or acrylate oligomer). The lower layer resin is, for example, a UV-curable resin. The lower layer resin used can be, for example, the same resin material as that used in the production method of the synthetic polymer film 34 previously described with reference to FIG. 6. The lower layer resin may not include fluorine. Although the lower layer resin may include fluorine, the fluorine content of the lower layer resin is preferably lower than the fluorine content of the upper layer resin. The lower layer resin is applied by, for example, a gravure method or a slot die method. The lower layer resin may be applied using a slit coater, a bar coater, or the like. The thickness of the lower layer resin film 36a' applied to the surface of the base film 42 is for example 3 μm to 30 μm, and preferably for example 5 μm to 7 μm. The viscosity of the lower layer resin is for example 50 cP to 200 cP, and preferably for example 100 cP.

The upper layer resin includes a fluorine-containing monomer 38. The fluorine-containing monomer 38 is, for example, a fluorine-containing acrylic resin. The fluorine-containing monomer 38 includes, for example, a fluorine-containing hydrocarbon chain 38c and an acrylate group 38t at the terminal. The fluorine-containing hydrocarbon chain 38c may include an ether bond. The fluorine-containing monomer 38 is preferably cured by UV irradiation. The upper layer resin is applied by, for example, a spray method, a gravure method or a slot die method. The upper layer resin may be applied using a slit coater, a bar coater, or the like. When a spray method is employed, the upper layer resin is applied to the moth-eye mold 100 using a swirl nozzle or ultrasonic nozzle. The thickness of the upper layer resin film 36b' applied to the moth-eye mold 100 is for example 0.1 μm to 5 μm, preferably for example 2 μm to 3 μm. The viscosity of the upper layer resin is, for example, 1 cP to 100 cP. When the upper layer resin is applied by a spray method, it is preferred that the viscosity of the upper layer resin is, for example, not more than 100 cP.

The upper layer resin further includes, for example, a reactive diluent. The reactive diluent used can be, for example, 4-acryloylmorpholine. The chemical structure formula of 4-acryloylmorpholine will be shown in the paragraph of [Chemical Formula 1]. 4-acryloylmorpholine includes an acryloyl group (H$_2$C=CH—C(=O)—) and includes nitrogen elements.

[Chemical Formula 1]

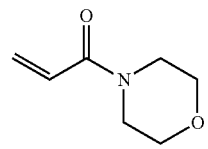

When a solvent is included in the lower layer resin, the step of evaporating the solvent (e.g., a heat treatment) is carried out before the step shown in FIG. 9(b). When a solvent is included in the upper layer resin, for example, the step of evaporating the solvent (e.g., a heat treatment) is carried out before the step shown in FIG. 9(b). Preferably, the lower layer resin and the upper layer resin do not include a solvent. When the lower layer resin and the upper layer resin do not include a solvent, the cost of using the solvent and the load on the environment (e.g., the smell emitted when the solvent is used) can be reduced. Further, the time required for the step of evaporating the solvent, the cost required for an apparatus for evaporation of the solvent, the room for such an apparatus, etc., can be suppressed.

When the lower layer resin of the synthetic polymer film 36 includes a solvent, the fluorine-containing monomer 38 included in the upper layer resin has a tendency to easily mix with the lower layer resin. Therefore, there is a concern that the fluorine elements might be unlikely to be unevenly present on the raised portion 36p side of the synthetic polymer film 36. When the lower layer resin of the synthetic polymer film 36 includes a solvent, there is a concern that insufficient drying of the solvent might deteriorate the adhesion between the base film 42 and the synthetic polymer film 36 (lower layer portion 36a).

Particularly for production of the synthetic polymer film 36 with the use of the moth-eye mold 100 in the form of a hollow cylinder, it is preferred that the upper layer resin does not include a solvent. Preferably, the viscosity of the upper layer resin which does not include a solvent is, for example, not more than 100 cP.

The moth-eye mold 100 may be provided with a mold releasing treatment. Specifically, a mold releasing agent may be applied to the inverted moth-eye structure of the moth-eye mold 100 before application of the upper layer resin. When the moth-eye mold 100 is provided with the mold releasing treatment, the fluorine-containing hydrocarbon chain 38c of the fluorine-containing monomer 38 is attracted by the mold releasing agent, so that the fluorine element content on the moth-eye mold 100 side of the upper layer resin film 36b' can be higher.

Then, as shown in FIG. 9(b), irradiation with ultraviolet light (UV) is carried out with the base film 42 being pressed against the moth-eye mold 100. When the base film 42 is pressed against the moth-eye mold 100, the lower layer resin film 36a' and the upper layer resin film 36b' are brought in contact with each other so that they mix with each other at the interface. A clear interface is not formed between the lower layer resin film 36a' and the upper layer resin film 36b' because the lower layer resin film 36a' and the upper layer resin film 36b' are not yet cured when the base film 42 is pressed against the moth-eye mold 100. The lower layer resin film 36a' and the upper layer resin film 36b', which have been mixed with each other, are irradiated with ultraviolet light, whereby the lower layer resin film 36a' and the upper layer resin film 36b' are cured.

By curing, the fluorine-containing monomers 38 react with the reactive diluent as shown in FIG. 9(c). The fluorine-containing monomers 38 also react with other acrylate monomers and/or acrylate oligomers (including ones included in the lower layer resin). The reference numeral of an acrylate group 38t after the reaction is suffixed with (r), which means that the acrylate group 38t has undergone the reaction. Thereafter, the moth-eye mold 100 is separated from the base film 42, whereby the synthetic polymer film 36 to which the inverted moth-eye structure of the moth-eye mold 100 is transferred is formed over the surface of the base film 42. The film 52 shown in FIG. 9(c) includes the base film 42 and the synthetic polymer film 36 formed on the base film 42. The synthetic polymer film 36 has a plurality of raised portions 36p over the surface. The plurality of raised portions 36p forms a moth-eye structure. When viewed in the normal direction of the synthetic polymer film 36, the two-dimensional size $D_p$ of the raised portions 36p is in the range of more than 20 nm and less than 500 nm. The raised portions 36p of the synthetic polymer film 36 may be generally equal to, for example, the raised portions 34p of the synthetic polymer film 34 in terms of two-dimensional size $D_p$, height $D_h$ and adjoining distance $S_{int}$. The two-dimensional size $D_p$, height $D_h$ and adjoining distance $D_{int}$ of the raised portions 36p of the synthetic polymer film 36 are determined according to the shape of recessed portions of the moth-eye mold 100 used in production of the synthetic polymer film 36.

The synthetic polymer film 36 includes, for example, a lower layer portion 36a which mainly includes the lower layer resin and an upper layer portion 36b which mainly includes the upper layer resin. The fluorine content of the upper layer portion 36b is higher than the fluorine content of the lower layer portion 36a. No clear interface is formed between the upper layer portion 36b and the lower layer portion 36a.

Since in the synthetic polymer film 36 the upper layer portion 36b includes the fluorine-containing monomer 38, grease, such as fingerprint, adhered to the synthetic polymer film 36 is unlikely to spread. Therefore, grease, such as fingerprint, adhered to the synthetic polymer film 36 is inconspicuous.

Further, grease, such as fingerprint, adhered to the synthetic polymer film 36 can be easily wiped away. Since grease can be easily wiped away, the probability of breaking the raised portions is low. Accordingly, it is estimated that the effect on the microbicidal activity is small.

As previously described with reference to FIG. 9, the production method of the synthetic polymer film 36 according to an embodiment of the present invention is a method for producing the synthetic polymer film 36 using a mold which includes a porous alumina layer, the porous alumina layer having an inverted moth-eye structure over its surface, the inverted moth-eye structure including a plurality of recessed portions whose two-dimensional size viewed in the normal direction of the surface is not less than 20 nm and less than 500 nm. The production method includes the following steps (a) to (c). Step (a) is the step of providing a mold and a work. Step (b) is the step of applying a first resin, which is a UV-curable resin, to a surface of the work and applying a second resin including a fluorine-containing monomer to a surface of the mold. Step (c) is the step of irradiating, with ultraviolet light, the first resin and the second resin which are interposed between the mold and the surface of the work so as to be in contact with each other, thereby curing the first resin and the second resin.

FIG. 10(b) is a graph schematically showing variations in the thickness direction (depth profiles) of the element concentrations of fluorine (F) and nitrogen (N) in the synthetic polymer film 36. In FIG. 10(b), the horizontal axis represents the depth from a surface of the synthetic polymer film 36 (a surface which has the plurality of raised portions 36p), i.e., the depth in the normal direction, and the vertical axis represents the element concentration (at %) of each element.

As the depth from the surface of the synthetic polymer film 36 increases, the fluorine element concentration of the synthetic polymer film 36 continuously (moderately) varies from the fluorine element concentration of the upper layer portion 36b to the fluorine element concentration of the lower layer portion 36a. The nitrogen element concentration of the synthetic polymer film 36 also continuously (moderately) varies from the nitrogen element concentration of the upper layer portion 36b to the nitrogen element concentration of the lower layer portion 36a as the depth from the surface of the synthetic polymer film 36 increases.

As the depth from the surface of the synthetic polymer film 36 increases, the concentration of each element may asymptotically approach the element concentration in the lower layer resin. A surface of the synthetic polymer film 36 opposite to the surface that has the plurality of raised portions 36p (also referred to as "a surface on the base film 42 side") has a composition generally equal to that of the lower layer resin. Herein, the composition of the surface on the base film 42 side of the synthetic polymer film 36 refers to the composition of a portion of the synthetic polymer film 36 which forms the surface on the base film 42 side. For example, the concentration of nitrogen elements included in the surface on the base film 42 side of the synthetic polymer film 36 refers to the concentration of nitrogen elements included in a portion of the synthetic polymer film 36 which forms the surface on the base film 42 side. It is estimated that, for example, a portion of the synthetic polymer film 36 corresponding to a ⅕ of the thickness $t_s$ of the synthetic polymer film 36 from the surface on the base film 42 side in the normal direction of the synthetic polymer film 36 has the same composition as that of the lower layer resin. Therefore, to determine the composition of the surface on the base film 42 side, the composition of the aforementioned portion of the synthetic polymer film 36 may be measured.

It can be estimated that a portion of the synthetic polymer film 36 corresponding to, for example, at least a ⅕ of the thickness $t_s$ of the synthetic polymer film 36 from the surface on the base film 42 side in the normal direction of the synthetic polymer film 36 does not substantially include the constituents of the upper layer resin but has the same composition as that of the lower layer resin. The reasons for such an estimation are now described. As previously described with reference to FIG. 9, in the production process of the synthetic polymer film 36, the lower layer resin film 36a' and the upper layer resin film 36b' are brought into contact with each other in pressing the base film 42 against the moth-eye mold 100. In the vicinity of the border between these resin films, the resins mix with each other due to mutual diffusion. However, the constituents included in the upper layer resin, particularly fluorine elements, are not necessarily diffused through the entirety of the lower layer resin film 36a'. This is because the fluorine elements have a tendency to migrate to the moth-eye mold 100. If the time interval between mutual contact of the lower layer resin film 36a' and the upper layer resin film 36b' and irradiation with ultraviolet light is short, the degree of the diffusion can be still smaller. The time interval between mutual contact of the lower layer resin film 36a' and the upper layer resin film 36b' and irradiation with ultraviolet light is, for example, 3 seconds to 5 seconds.

The variation of the element concentration of each element in the synthetic polymer film 36 with respect to the thickness direction is, as a matter of course, not limited to the illustrated example. For example, although the lower layer portion 36a does not include silicon elements or fluorine elements in the illustrated example, the element concentrations of silicon elements and fluorine elements can be varied by arbitrarily selecting the materials of the lower layer resin. The lower layer resin may include a fluoric lubricant and/or a silicone lubricant. When the upper layer resin includes a reactive diluent, the upper layer portion 36b includes, for example, nitrogen elements and an acryloyl group.

The synthetic polymer films 35, 36 can have a shape similar to those of the synthetic polymer films 34A and 34B shown in FIGS. 1(a) and 1(b) according to the surficial nanostructures of the moth-eye mold 100 used.

described with reference to FIG. 6. As the acrylic resin (acrylate monomer or acrylate oligomer) for production of the lower layer resin film 35a of the synthetic polymer film 35, resins A and B specified in Table 1 below were used. Table 1 shows the compositions of the respective resins ("%" in Table 1 means mass %). The chemical structure formulae of acrylic resins I to III will be shown in the paragraphs of [Chemical Formula 2] to [Chemical Formula 4], respectively.

TABLE 1

| | Acrylic Resin I | Acrylic Resin II | Acrylic Resin III | |
|---|---|---|---|---|
| | NK Oligo UA-7100 (manufactured by Shin Nakamura Chemical Co., Ltd.) | NK Ester A-TMM-3LM-N (manufactured by Shin Nakamura Chemical Co., Ltd.) | 4-HBA (manufactured by Nippon Kasei Chemical Company Limited) | Photoinitiator IRGACURE 819 (manufactured by BASF) |
| Resin A | 39.80% | 29.85% | 29.85% | 0.49% |
| Resin B | 99.29% | — | — | 0.71% |

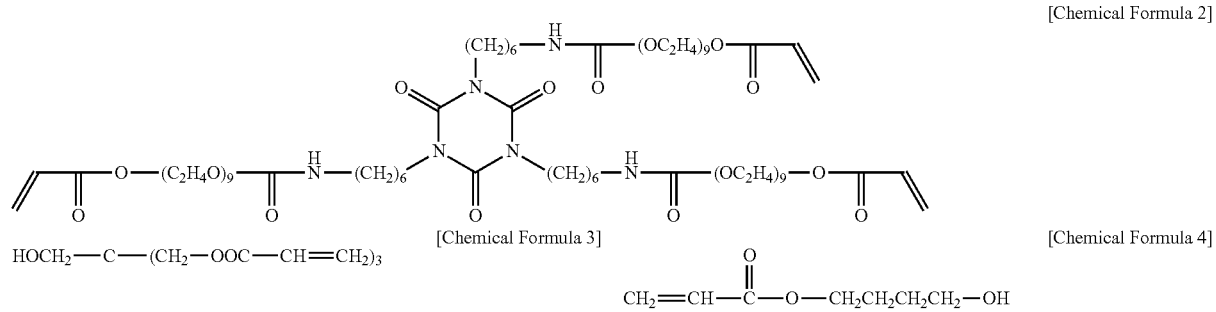

[Chemical Formula 2]

[Chemical Formula 3]

[Chemical Formula 4]

Hereinafter, it will be explained with experimental examples that the synthetic polymer films 35, 36 of an embodiment of the present invention have microbicidal ability.

[Synthetic Polymer Film]

Sample films No. 1 to No. 6 were provided. Sample films No. 1 and No. 2 have the same configuration as that of the film 51 shown in FIG. 8(b). Sample films No. 3 and No. 4 have the same configuration as that of the film 52 shown in FIG. 9(c). The shape of the synthetic polymer films 35 and 36 of sample films No. 1 to No. 4 are the same as that of the synthetic polymer film 34A. Sample films No. 5 and No. 6 have the same configuration as that of the film 50A shown in FIG. 1(a).

Sample films No. 1 and No. 2 were produced by the production method of the synthetic polymer film 35 which has previously been described with reference to FIG. 8. First, the lower layer resin film 35a of the synthetic polymer film 35 was produced by the production method of the synthetic polymer film 34 which has previously been Acrylic resin I is urethane acrylate (manufactured by Shin Nakamura Chemical Co., Ltd., product name: UA-7100, molecular weight: 1908) and includes nitrogen elements. The chemical formula shown in the paragraph of [Chemical Formula 2] is based on estimation. The molecular weight is a value which is based on the chemical formula shown in the paragraph of [Chemical Formula 2]. Acrylic resins II and III do not include a nitrogen element. Acrylic resin II is pentaerythritol triacrylate (trimester about: 57%) (manufactured by Shin Nakamura Chemical Co., Ltd.: A-TMM-3LM-N, molecular weight: 298). Acrylic resin III is 4 hydroxybutyl acrylate (manufactured by Nippon Kasei Chemical Company Limited: 4-HBA, molecular weight: 144). The polymerization initiator used was IRGACURE819 (molecular weight: 418.5) manufactured by BASF.

The nitrogen element concentration of resin A was 0.430 at %. The nitrogen element concentration of resin B was 1.035 at %. These nitrogen element concentration values were calculated based on the composition and the chemical formulae for respective ones of resins A and B. Note that, however, nitrogen elements which are constituents of the tertiary amines were not counted for the following reason. The nitrogen elements which are constituents of the tertiary amines are less basic, and therefore, it is estimated that these nitrogen elements are unlikely to contribute to the microbicidal ability of the synthetic polymer film. Further, in resin A and resin B, the nitrogen elements which are constituents of the tertiary amines form a ring. The nitrogen elements that form a ring are present at a position relatively distant from the surface of the synthetic polymer film and are widely distant from a microorganism. Therefore, it is estimated that the contribution of these nitrogen elements to the microbicidal ability of the synthetic polymer film is small. The present applicant found, in International Application 3, that the evaluation results as to the antimicrobial ability and the microbicidal ability of the synthetic polymer film seem to have a correlation with the nitrogen element concentration calculated exclusive of the nitrogen elements which are constituents of the tertiary amines rather than the nitrogen element concentration calculated inclusive of the nitrogen elements which are constituents of the tertiary amines.

The number of moles of EO units included in one gram of resin A is 0.0056. The number of moles of EO units included in one gram of resin B is 0.0141.

Resin B was dissolved into MEK (manufactured by Maruzen Petrochemical Co., Ltd.), resulting in a solution, 70 mass % of which was solid. The resultant solution was applied onto the base film 42A, and MEK was removed by heating, whereby a film having a thickness of about 27 μm was obtained. Resin A was applied to the base film 42 without being dissolved into a solvent, whereby a film having a thickness of about 30 μm was obtained. Note that the base film 42 used was a PET film (A4300 manufactured by TOYOBO CO., LTD.) having a thickness of about 50 μm. Thereafter, a synthetic polymer film 34A which had the moth-eye structure over the surface (i.e., the lower layer resin film 35a) was produced using the moth-eye mold 100A through the same process as that described with reference to FIG. 6. The exposure amount was about 200 mJ/cm$^2$. UV irradiation was carried out, by using an UV lamp (Light Hammer6 J6P3 manufactured by Fusion UV Systems; maximum power: 200 W/cm), for 30 seconds at the power level of 45%. In the lower layer resin film 35a of sample films No. 1 and No. 2, $D_p$ was about 200 nm, $D_{int}$ was about 200 nm, and $D_h$ was about 150 nm.

Then, an upper layer resin film 35b was formed. After an oxygen ($O_2$) plasma treatment was performed on the surface of the cured lower layer resin film 35a, a film of silicon dioxide ($SiO_2$) was formed on the lower layer resin film 35a by radio frequency (RF) sputtering. The thickness of the silicon dioxide film was about 10 nm. The upper layer resin was deposited on the silicon dioxide film by induction heating (vacuum degree: $1\times10^{-1}$ to $1\times10^{-3}$ Pa), whereby an upper layer resin film 35b was formed. The upper layer resin used was a fluorine-containing mold releasing agent (OPTOOL DSX manufactured by DAIKIN INDUSTRIES, LTD). The thickness of the upper layer resin film 35b was not more than 10 nm. In the synthetic polymer film 35 of sample films No. 1 and No. 2, $D_p$ was about 200 nm, $D_{int}$ was about 200 nm, and $D_h$ was about 150 nm.

Sample films No. 3 and No. 4 were produced by the method previously described with reference to FIG. 9. A lower layer resin film 36a' was formed on a base film 42 using the lower layer resin. For sample film No. 3, the lower layer resin used was resin A. For sample film No. 4, the lower layer resin used was resin B. The thickness of the lower layer resin film 36a' was about 7 μm. The base film 42 used was the same as that used in sample films No. 1 and No. 2. On the inverted moth-eye structure of the moth-eye mold 100A to which a mold releasing treatment was provided in advance, an upper layer resin film 36b' was formed by a spray method. The mold releasing treatment was carried out by applying a mold releasing agent (OPTOOL DSX manufactured by DAIKIN INDUSTRIES, LTD) by an immersion method. The thickness of the upper layer resin film 36b' was about 1.3 μm. The upper layer resin film 36b' was formed of a resin material prepared by diluting DAC-HP 5-fold with a reactive diluent (ACMO manufactured by KJ Chemicals Corporation). The "DAC-HP" refers to an active ingredient included in OPTOOL DAC-HP manufactured by DAIKIN INDUSTRIES, LTD. Commercially-available OPTOOL DAC-HP manufactured by DAIKIN INDUSTRIES, LTD is prepared by diluting the active ingredient 5-fold with a fluoric solvent (i.e., the active ingredient is 20 wt %).

Irradiation with ultraviolet light (UV) was carried out with the base film 42 being pressed against the moth-eye mold 100A. The UV irradiation conditions were the same as those for sample films No. 1 and No. 2.

Sample films No. 5 and No. 6 have the same configuration as that of the synthetic polymer film 34A. That is, sample films No. 5 and No. 6 only include the lower layer resin film 35a of the synthetic polymer film 35, but do not include the upper layer resin film 35b. Sample films No. 5 and No. 6 were produced using resin A and resin B, respectively, by the same method as that for the lower layer resin film 35a of sample films No. 1 and No. 2.

Sample films No. 1 to No. 6 were evaluated as described in the following section.

[Evaluation of Microbicidal Ability and Antimicrobial Ability]

The microbicidal ability of the sample films was evaluated as follows:
1. Beads with frozen *P. aeruginosa* bacteria (purchased from National Institute of Technology and Evaluation) were immersed in a broth at 37° C. for 24 hours, whereby the *P. aeruginosa* bacteria were thawed;
2. Centrifugation (3000 rpm, 10 minutes);
3. The supernatant of the broth was removed;
4. Sterilized water was added, and the resultant solution was stirred and thereafter subjected to centrifugation again;
5. Steps 2 to 4 were repeated three times to obtain an undiluted bacterial solution (the bacteria count was of the order of 1E+08 CFU/mL);
6. Bacterial dilution A (the bacteria count was of the order of 1E+06 CFU/mL) was prepared.

Bacterial Dilution A: Undiluted Bacterial Solution 100 μL+Sterilized Water 9.9 mL;
7. Bacterial dilution B (the bacteria count was of the order of 1E+05 CFU/mL) was prepared by adding, to bacterial dilution A, an NB culture medium (nutrient broth medium E-MC35 manufactured by Eiken Chemical Co., Ltd.) as a nutrient source at the concentration of 1/500 and diluting the resultant mixture 10-fold (in accordance with JIS Z2801 5.4a)).

Bacterial Dilution B: Bacterial Dilution A 1 mL+Sterilized Water 8.98 mL+NB Culture Medium 20 μL;
8. A 400 μL drop of bacterial dilution B (the bacteria count in the bacterial dilution B at this point in time is also referred to as "initial bacteria count") was placed on each of the sample films. A cover (e.g., cover glass) was placed over the bacterial dilution B to adjust the amount of the bacterial dilution B per unit area.

Here, the initial bacteria count on sample films No. 1 and No. 2 was 1.0E+05 CFU/mL, the initial bacteria count on sample film No. 3 was 3.3E+05 CFU/mL, the initial bacteria count on sample film No. 4 was 3.5E+05 CFU/mL, and the initial bacteria count on sample films No. 5 and No. 6 was 4.3E+05 CFU/mL;

9. The samples were left in an environment where the temperature was 37° C. and the relative humidity was 100% for a predetermined time period (time period: 4 hours or 24 hours);

10. The entire sample film with the bacterial dilution B and 9.6 mL sterilized water were put into a filter bag. The sample film was rubbed with hands over the filter bag to sufficiently wash away the bacteria from the sample film. The post-wash solution in the filter bag was a 25-fold dilution of the bacterial dilution B. This post-wash solution is also referred to as "bacterial dilution B2". The bacteria count of the bacterial dilution B2 is to be of the order of 1E+04 CFU/mL if the bacteria count in the bacterial dilution B does not increase or decrease;

11. The bacterial dilution B2 was diluted 10-fold, whereby bacterial dilution C was prepared. Specifically, the bacterial dilution C was prepared by putting 120 μL of the post-wash solution (bacterial dilution B2) into 1.08 mL sterilized water. The bacteria count of the bacterial dilution C is to be of the order of 1E+03 CFU/mL if the bacteria count in the bacterial dilution B does not increase or decrease;

12. The bacterial dilution C was diluted 10-fold in the same way as that for preparation of the bacterial dilution C, whereby bacterial dilution D was prepared. The bacteria count of the bacterial dilution D is to be of the order of 1E+02 CFU/mL if the bacteria count in the bacterial dilution B does not increase or decrease. Further the bacterial dilution D was diluted 10-fold, whereby bacterial dilution E was prepared. The bacteria count of the bacterial dilution E is to be of the order of 1E+01 CFU/mL if the bacteria count in the bacterial dilution B does not increase or decrease;

13. 1 mL drops of the bacterial dilution B2 and the bacterial dilutions C to E were placed on Petrifilm™ media (product name: Aerobic Count Plate (AC), manufactured by 3M). The bacteria were cultured at 37° C. with the relative humidity of 100%. After 48 hours, the number of bacteria in the bacterial dilution B2 was counted.

Note that, although in JIS 22801 5.6h) a phosphate-buffered saline is used in preparation of a diluted solution, sterilized water was used herein. It was verified that the microbicidal effect which is attributed to the physical structure and chemical properties of the surface of the sample films can be examined even when sterilized water is used.

When the antibacterial activity value determined from the bacteria count on a sample film after the culture of 24 hours in accordance with JIS Z 2801 was not less than 2.0 (the death rate was not less than 99%), the sample film was judged to have an antimicrobial effect. The reference film used was a base film (PET film). The antibacterial activity value is the logarithmic value of the value obtained by dividing the bacteria count after the culture of 24 hours on the PET film by the bacteria count after the culture of 24 hours on each sample film. In calculation of the antibacterial activity value of sample films No. 1 and No. 2, the data of PET1 were used. In calculation of the antibacterial activity value of sample film No. 3, the data of PET2 were used. In calculation of the antibacterial activity value of sample film No. 4, the data of PET3 were used. In calculation of the antibacterial activity value of sample films No. 5 and No. 6, the data of PET4 were used.

Figure 11:
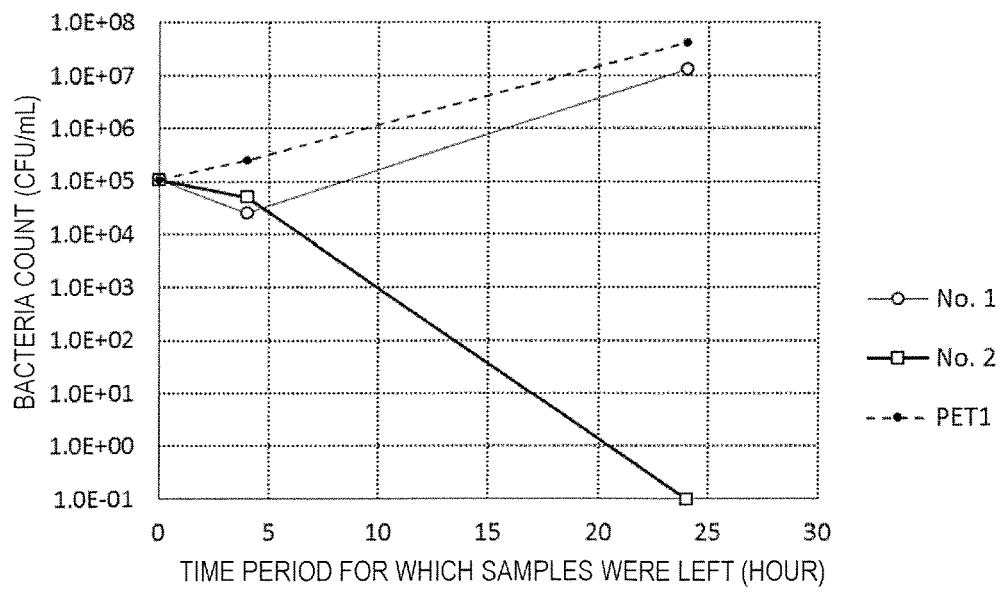
FIG. 11 is a graph showing the evaluation results as to the microbicidal ability.
Figure 12:
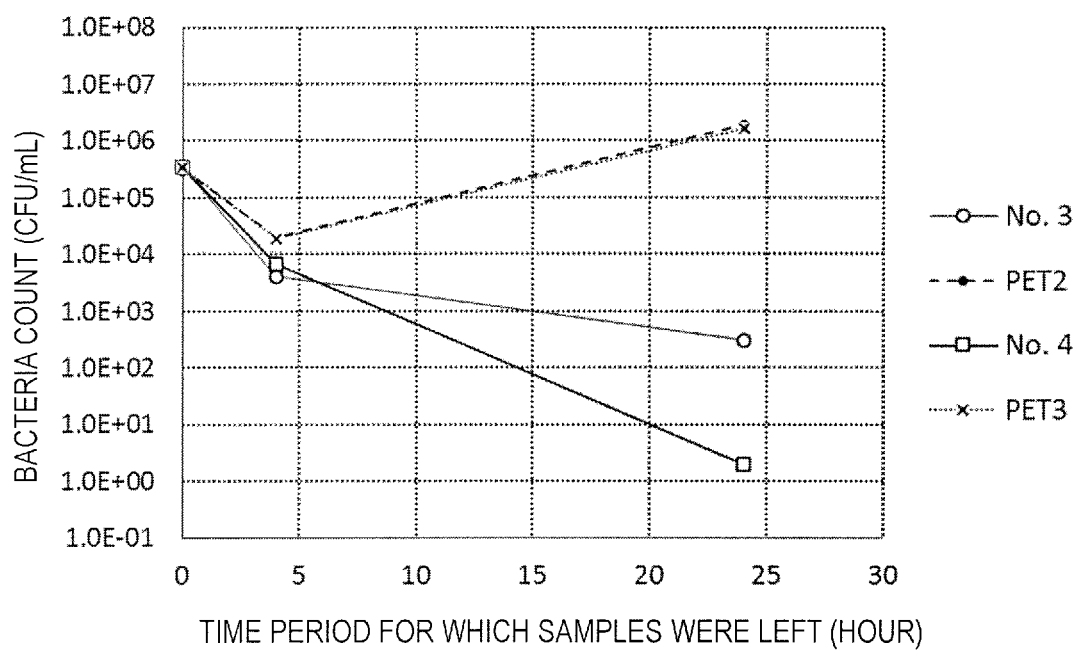
FIG. 12 is a graph showing the evaluation results as to the microbicidal ability.
Figure 13:
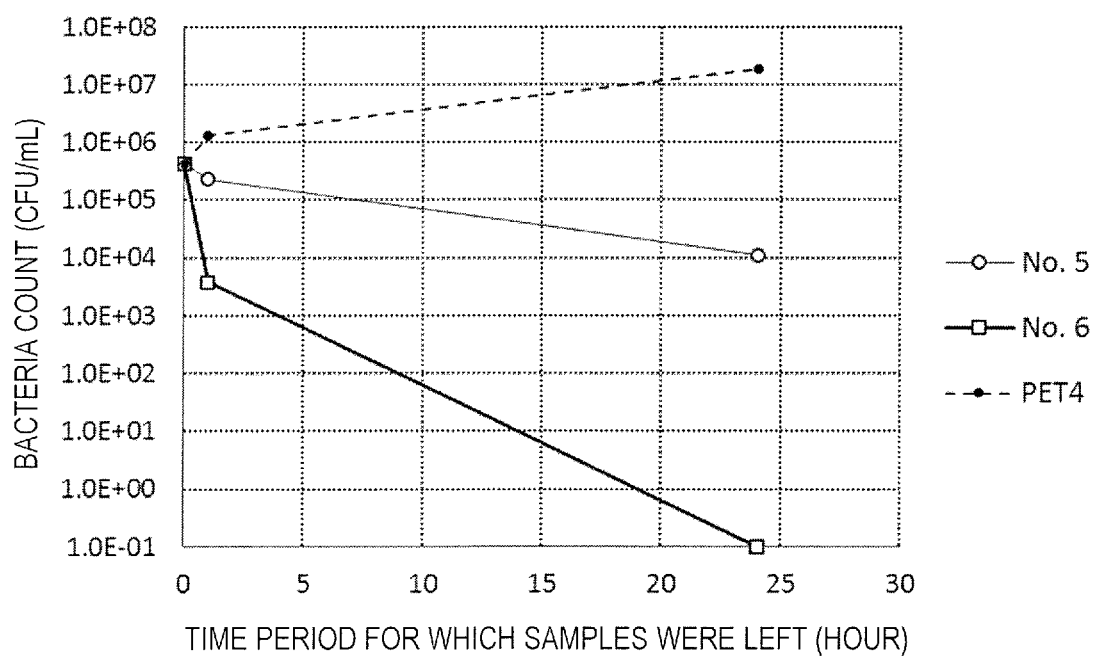
FIG. 13 is a graph showing the evaluation results as to the microbicidal ability.

FIG. 11 to FIG. 13 are graphs showing the evaluation results as to the microbicidal ability. In FIG. 11 to FIG. 13, the horizontal axis represents the time period for which the sample films were left (hour), and the vertical axis represents the bacteria count in bacterial dilution B2 (CFU/mL). The initial bacteria count is plotted as the value for the time period of 0 hour. Note that, in FIG. 11 to FIG. 13, when the bacteria count is 0 (N.D.), it is plotted as 0.1 for the sake of visibility. Table 2 presented below shows the bacteria count after the culture and the antibacterial activity value.

TABLE 2

| Sample Film | Bacteria Count (4 hours/1 hour*) | Bacteria Count (24 hours) | Antibacterial Activity Value |
|---|---|---|---|
| No. 1 | 2.5E+04 | 1.30E+07 | 0.5 |
| No. 2 | 5.0E+04 | N.D. | 7.6 |
| PET1 | 2.5E+05 | 4.25E+07 | — |
| No. 3 | 4.1E+03 | 3.0E+02 | 3.8 |
| PET2 | 2.0E+04 | 1.9E+06 | — |
| No. 4 | 6.7E+03 | 2.0E+00 | 5.9 |
| PET3 | 1.9E+04 | 1.6E+06 | — |
| No. 5 | 2.3E+05* | 1.1E+04 | 3.2 |
| No. 6 | 3.8E+03* | N.D. | 5.8 |
| PET4 | 1.3E+06* | 1.8E+07 | — |

As seen from FIG. 11 to FIG. 13 and Table 2, the sample films, except for sample film No. 1, had antibacterial activity values of not less than 2.0 and had antimicrobial ability. Herein, with reference to sample film No. 6 on which no bacteria was detected after being left for 24 hours, it is determined that the film had a microbicidal effect when a film had an antibacterial activity value of not less than 5.8.

Sample films No. 2, No. 4 and No. 6, in which resin B was used, had antibacterial activity values of not less than 5.8, and therefore, it can be said that sample films No. 2, No. 4 and No. 6 had microbicidal ability. It can be said that, compared to the microbicidal ability of sample film No. 6 that did not include the upper layer resin film, the microbicidal ability of sample film No. 2 was not substantially inferior even though the upper layer resin film was further included in sample film No. 2. (The antibacterial activity value increased from 5.8 to 7.6.) It can be said that the microbicidal ability of sample film No. 4 that was formed of resin B (the lower layer resin) and the upper layer resin was not substantially inferior to sample film No. 6 that was formed of resin B. (The antibacterial activity value slightly increased from 5.8 to 5.9, i.e., did not substantially change.)

Among sample films No. 1, No. 3 and No. 5 in which resin A was used, the sample films except for sample film No. 1 had an antibacterial activity value of not less than 2.0, and thus, it can be said that they had antimicrobial ability. It can be understood that the antimicrobial ability of sample film No. 5 which did not include the upper layer resin film was suppressed when the upper layer resin film was included as in sample film No. 1. (The antibacterial activity value decreased from 3.2 to 0.5). However, the microbicidal ability of sample film No. 3 that was formed of resin A (the lower layer resin) and the upper layer resin was not substantially inferior to sample film No. 5 that was formed of resin A. (The antibacterial activity value increased from 3.2 to 3.8.)

In view of the foregoing, an example of the method for producing a synthetic polymer film which includes fluorine elements without deteriorating the microbicidal ability of the synthetic polymer film is as follows. For example, a synthetic polymer film 35 is formed by forming an upper layer resin film 35b which includes a fluorine-containing mold releasing agent 37 on a synthetic polymer film 34 which has excellent microbicidal ability. Preferably, the lower layer resin film 35a of the synthetic polymer film 35 includes, for example, a urethane acrylate structure. In order that the synthetic polymer film 35 has microbicidal ability, it is preferred that the lower layer resin film 35a includes, for example, nitrogen elements (exclusive of nitrogen elements which are constituents of the tertiary amines) in the proportion of not less than 1.035 at %. That is, in order that the synthetic polymer film 35 has microbicidal ability, it is preferred that, for example, nitrogen elements (exclusive of nitrogen elements which are constituents of the tertiary amines) are included in the proportion of not less than 1.035 at % at a surface opposite to the surface that has a plurality of raised portions 35p (also referred to as "a surface on the base film 42 side"). Herein, the composition of the surface on the base film 42 side of the synthetic polymer film 35 refers to the composition of a portion of the synthetic polymer film 35 which forms the surface on the base film 42 side, and is equal to the composition of the lower layer resin film 35a.

Alternatively, forming the synthetic polymer film 36 under the conditions that the lower layer resin is used as the resin for formation of a synthetic polymer film 34 which has excellent microbicidal ability and that the upper layer resin which includes a fluorine-containing monomer is used together also enables formation of a synthetic polymer film which includes fluorine elements without deteriorating the microbicidal ability of the synthetic polymer film. Preferably, the lower layer resin of the synthetic polymer film 36 include, for example, a urethane acrylate structure. In order that the synthetic polymer film 36 has antimicrobial ability, it is preferred that the lower layer resin of the synthetic polymer film 36 includes, for example, nitrogen elements (exclusive of nitrogen elements which are constituents of the tertiary amines) in the proportion of not less than 0.430 at %. In order that the synthetic polymer film 36 has microbicidal ability, it is preferred that the lower layer resin of the synthetic polymer film 36 includes, for example, nitrogen elements (exclusive nitrogen elements which are constituents of the tertiary amines) in the proportion of not less than 1.035 at %. That is, in order that the synthetic polymer film 36 has antimicrobial ability, it is preferred that, for example, nitrogen elements (exclusive of nitrogen elements which are constituents of the tertiary amines) are included in the proportion of not less than 0.430 at % at the surface on the base film 42 side. In order that the synthetic polymer film 36 has microbicidal ability, it is preferred that, for example, nitrogen elements (exclusive of nitrogen elements which are constituents of the tertiary amines) are included in the proportion of not less than 1.035 at % at the surface on the base film 42 side.

As described above, bringing a liquid into contact with the surface of a synthetic polymer film according to an embodiment of the present invention enables sterilization of the liquid. Likewise, bringing a gas into contact with the surface of a synthetic polymer film according to an embodiment of the present invention enables sterilization of the gas.

In a synthetic polymer film of an embodiment of the present invention, grease, such as fingerprint, adhered to the surface is inconspicuous. Therefore, the synthetic polymer film can be suitably used in touch panels and display panels which are to be touched by hands when used. For example, a synthetic polymer film which has a microbicidal surface may be applied to display panels and touch panels placed in hospitals or public places, which can be touched by a large number of unspecified users.

[Evaluation of Anti-Smear Properties]

Sample films No. 7 to No. 10 which include a synthetic polymer film of an embodiment of the present invention were evaluated as to the anti-smear properties (inconspicuousness of grease adhered to the surface, easiness in wiping grease, and abrasion resistance).

Sample film No. 7 was produced by the same method as that for sample films No. 1 and No. 2. That is, sample film No. 7 has the same configuration as the film 51 shown in FIG. 8(b). Note that, however, resin C specified in Table 3 below was used as the acrylic resin (acrylate monomer or acrylate oligomer) for production of the lower layer resin film 35a of the synthetic polymer film 35.

Sample film No. 8 was produced using resin C by the same method as that for sample films No. 5 and No. 6. That is, sample film No. 8 has the same configuration as the film 50A shown in FIG. 1(a).

Sample film No. 9 was produced by the same method as that for sample films No. 3 and No. 4. That is, sample film No. 9 has the same configuration as the film 52 shown in FIG. 9(c). Note that, however, resin D specified in Table 3 below was used as the lower layer resin.

Sample film No. 10 was produced using resin D by the same method as that for sample films No. 5 and No. 6. That is, sample film No. 10 has the same configuration as the film 50A shown in FIG. 1(a).

Table 3 shows the compositions of resin C and resin D ("%" in Table 3 means mass %). The chemical structure formula of acrylic resin IV will be shown in the paragraph of [Chemical Formula 5].

TABLE 3

|  | Acrylic Resin I NK Oligo UA-7100 (manufactured by Shin Nakamura Chemical Co., Ltd.) | Acrylic Resin II NK Ester A-TMM-3LM-N (manufactured by Shin Nakamura Chemical Co., Ltd.) | Acrylic Resin IV NK Ester ATM-35E (manufactured by Shin Nakamura Chemical Co., Ltd.) | Photoinitiator IRGACURE819 (manufactured by BASF) | Photoinitiator LUCIRIN TPO (manufactured by BASF) |
|---|---|---|---|---|---|
| Resin C | 30.9% | 27.4% | 38.8% | 1.5% | 1.5% |
| Resin D | 31.0% | 27.5% | 40.0% | 1.5% | — |

[Chemical Formula 5]

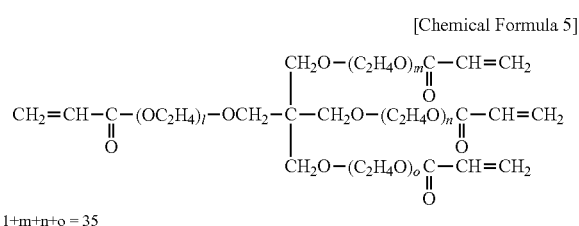

l+m+n+o = 35

Each of the obtained sample films No. 7 to No. 10 were evaluated as to inconspicuousness of grease adhered to the surface, easiness in wiping grease, and abrasion resistance. The evaluation was carried out as described in the following paragraphs. The evaluation results are shown in Table 4 below.

Inconspicuousness of grease adhered to the surface was evaluated based on whether or not an oil content adhered to the surface of a sample spreads with the passage of time. Specifically, a black acrylic plate (manufactured by MITSUBISHI RAYON CO., LTD., product name: ACRYLITE (registered trademark) EX-502) was attached to the base film of each sample. NIVEA cream (registered trademark, manufactured by Nivea-Kao, Co., Ltd.) was adhered to the surface of each sample. The samples were left in an environment at the temperature of 25° C. and the humidity of 40% to 60% for three days. The spread of the oil content was visually observed in an environment with the illuminance of 100 lx (fluorescent lamp), and it was determined whether or not there was spread of the oil content. In Table 4, as for "Inconspicuousness of Grease", "○" means that there was no spread of the oil content, and "x" means that there was spread of the oil content.

Easiness in wiping grease was evaluated based on whether or not an oil content adhered to the surface of samples can be easily wiped away. Specifically, first, NIVEA cream (registered trademark) manufactured by Nivea-Kao, Co., Ltd. was adhered to the surface of each sample. The samples were left in an environment at the temperature of 25° C. and the humidity of 40% to 60% for three days. Thereafter, each sample was wiped 50 times in one direction using nonwoven fabric (manufactured by KB SEIREN, LTD., product name: Savina (registered trademark)). It was visually observed in an environment with the illuminance of 100 lx (fluorescent lamp) whether or not the oil content was wiped away. In Table 4, as for "Easiness in Wiping Grease", "○" means that the oil content was almost completely wiped away, and "x" means that the oil content was scarcely wiped away.

Abrasion resistance was evaluated based on the steel wool (SW) resistance for each sample. The steel wool resistance was evaluated by rubbing the surface of each sample with steel wool (manufactured by Nippon Steel Wool Co., Ltd., product name: #0000, fiber center diameter: about 0.012 mm) on which a predetermined weight was placed and determining the minimum weight at which scratches were made. In the rubbing test, the surface of the samples was rubbed with the steel wool using a surface property tester (manufactured by Shinto Scientific Co., Ltd., product name: 14FW) under the conditions that the stroke width was 30 mm, the speed was 100 mm/s, and the rubbing count was 10 reciprocations. The presence/absence of scratches was visually observed in an environment with the illuminance of 100 lx (fluorescent lamp). In Table 4, as for "Abrasion Resistance", "○" means that the minimum weight was not less than 100 g, and "x" means that the minimum weight was less than 100 g.

TABLE 4

| Sample Film | Inconspicuousness of Grease | Easiness in Wiping Grease | Abrasion Resistance |
|---|---|---|---|
| No. 7 | ○ | x | x |
| No. 8 | x | x | x |
| No. 9 | ○ | ○ | ○ |
| No. 10 | x | x | x |

As seen from Table 4, sample films No. 7 and No. 9 are better than sample films No. 8 and No. 10 in inconspicuousness of grease adhered to the surface of the synthetic polymer film. Further, sample film No. 9 is better in easiness in wiping grease and abrasion resistance.

Herein, sample films No. 1 to No. 6 were not evaluated as to the anti-smear properties. However, it is supposed that the similar evaluation results will be obtained as those of sample films No. 7 to No. 10. That is, it is supposed that sample films No. 1 to No. 4 are better than sample films No. 5 and No. 6 in inconspicuousness of grease, such as fingerprint, adhered to the surface of the synthetic polymer film. Further, sample films No. 3 and No. 4 are capable of easy wiping away of grease and better in abrasion resistance.

A synthetic polymer film according to an embodiment of the present invention is suitably applicable to uses of suppressing generation of slime on a surface which is in contact with water, for example. For example, the synthetic polymer film is attached onto the inner walls of a water container for a humidifier or ice machine, whereby generation of slime on the inner walls of the container can be suppressed. The slime is attributed to a biofilm which is formed of extracellular polysaccharide (EPS) secreted from bacteria adhering to the inner walls and the like. Therefore, killing the bacteria adhering to the inner walls and the like enables suppression of generation of the slime.

As described above, bringing a liquid into contact with the surface of a synthetic polymer film according to an embodiment of the present invention enables sterilization of the liquid. Likewise, bringing a gas into contact with the surface of a synthetic polymer film according to an embodiment of the present invention enables sterilization of the gas. In general, microorganisms have such a surface structure that they can easy adhere to the surface of an object in order to increase the probability of contact with organic substances which will be their nutrients. Therefore, when a liquid or gas which contains microorganisms is brought into contact with a microbicidal surface of a synthetic polymer film according to an embodiment of the present invention, the microorganisms are likely to adhere to the surface of the synthetic polymer film, and therefore, on that occasion, the liquid or gas is subjected to the microbicidal activity.

Although the microbicidal activity of a synthetic polymer film according to an embodiment of the present invention against *P. aeruginosa* that is a Gram-negative bacteria has been described in this section, the synthetic polymer film has a microbicidal activity not only on Gram-negative bacteria but also on Gram-positive bacteria and other microorganisms. One of the characteristics of the Gram-negative bacteria resides in that they have a cell wall including an exine. The Gram-positive bacteria and other microorganisms (including ones that do not have a cell wall) have a cell membrane. The cell membrane is formed by a lipid bilayer as is the exine of the Gram-negative bacteria. Therefore, it is estimated that the interaction between the raised portions of the surface of the synthetic polymer film according to an embodiment of the present invention and the cell membrane is basically the same as the interaction between the raised portions and the exine.

INDUSTRIAL APPLICABILITY

A synthetic polymer film which has a microbicidal surface according to an embodiment of the present invention is applicable to various uses including, for example, uses for sterilization of surfaces of kitchen and bathroom facilities. The synthetic polymer film which has a microbicidal surface according to an embodiment of the present invention can be produced at low cost.

REFERENCE SIGNS LIST 34A, 34B, 35, 36 synthetic polymer film
34Ap, 34Bp, 35p, 36p raised portion
42A, 42B base film
50A, 50B film
100, 100A, 100B moth-eye mold

The invention claimed is:

1. A synthetic polymer film having a first surface which has a plurality of raised portions, wherein:
  a two-dimensional size of the plurality of raised portions is in a range of greater than 20 nm and less than 500 nm when viewed in a normal direction of the synthetic polymer film, the first surface having a microbicidal effect;
  the synthetic polymer film includes a fluorine element in a profile that a fluorine content is not constant in a thickness direction but is higher in a first portion closer to the plurality of raised portions than in a second portion farther from the plurality of raised portions;
  the first portion includes a third portion that is formed from a first photocurable resin, the first photocurable resin including a fluorine-containing acrylic monomer, an acryloyl group-containing monomer, and no urethane acrylate monomer;
  the first portion further includes a fourth portion that is formed from the first photocurable resin and a second photocurable resin, the second photocurable resin including a urethane acrylate monomer;
  the second portion is formed from the second photocurable resin;
  the second portion and the fourth portion are in contact with each other;
  the entirety of the plurality of raised portions is included in the first portion;
  the entirety of the plurality of raised portions is included in the third portion;
  the third portion and the fourth portion are in contact with each other; and
  the fourth portion is between the third portion and the second portion in the thickness direction.

2. The synthetic polymer film of claim 1, wherein the fluorine content continuously varies in the thickness direction.

3. The synthetic polymer film of claim 1, wherein a nitrogen content continuously varies in the thickness direction.

4. The synthetic polymer film of claim 1, wherein the synthetic polymer film further includes, at a second surface opposite to the first surface, a nitrogen element which is not a constituent of a tertiary amine in a proportion of not less than 0.430 at %.

5. The synthetic polymer film of claim 1, wherein the synthetic polymer film further includes, at a second surface opposite to the first surface, a nitrogen element which is not a constituent of a tertiary amine in a proportion of not less than 1.035 at %.

6. A method for sterilizing a gas or liquid, comprising bringing the gas or liquid into contact with the first surface of the synthetic polymer film as set forth in claim 1.

7. The synthetic polymer film of claim 1, wherein the second photocurable resin includes an acrylate monomer which has three or more functional groups, and
  a value of a molecular weight of the acrylate monomer divided by a number of the functional groups of the acrylate monomer is equal to or more than 473.

8. The synthetic polymer film of claim 1, wherein the first surface is included in the third portion.

9. The synthetic polymer film of claim 1, wherein the third portion includes no urethane acrylate structure.

10. The synthetic polymer film of claim 1, wherein the fluorine content is higher in the third portion than in the fourth portion, and
  the second portion does not include any fluorine element.

11. The synthetic polymer film of claim 1, wherein the acryloyl group-containing monomer comprises acryloylmorpholine.

12. A synthetic polymer film having a first surface which has a plurality of raised portions, wherein:
  a two-dimensional size of the plurality of raised portions is in a range of greater than 20 nm and less than 500 nm when viewed in a normal direction of the synthetic polymer film, the first surface having a microbicidal effect;
  a logarithmic value of a value obtained by dividing a bacteria count after culturing for 24 hours on a polyethylene terephthalate (PET) film by a bacteria count after culturing for 24 hours on the first surface is more than 3.8;
  the synthetic polymer film includes a fluorine element in a profile that a fluorine content is not constant in a thickness direction but is higher in a first portion closer to the plurality of raised portions than in a second portion farther from the plurality of raised portions;
  the first portion includes a third portion that is formed from a first photocurable resin, the first photocurable resin including a fluorine-containing acrylic monomer, an acryloyl group-containing monomer, and no urethane acrylate monomer;
  the first portion further includes a fourth portion that is formed from the first photocurable resin and a second photocurable resin, the second photocurable resin including a urethane acrylate monomer;
  the second portion is formed from the second photocurable resin;
  the second portion and the fourth portion are in contact with each other;
  the entirety of the plurality of raised portions is included in the first portion;
  the synthetic polymer film includes, at a second surface opposite to the first surface, a nitrogen element which is not a constituent of a tertiary amine in a proportion of not less than 1.035 at %;
  the entirety of the plurality of raised portions is included in the third portion;

the third portion and the fourth portion are in contact with each other; and the fourth portion is between the third portion and the second portion in the thickness direction.

13. The synthetic polymer film of claim 12, wherein the logarithmic value is more than 3.8 and not more than 5.9.

14. The synthetic polymer film of claim 12, wherein the fluorine content continuously varies in the thickness direction.

15. The synthetic polymer film of claim 12, wherein a nitrogen content continuously varies in the thickness direction.

16. A method for sterilizing a gas or liquid, comprising bringing the gas or liquid into contact with the first surface of the synthetic polymer film as set forth in claim 12.

17. The synthetic polymer film of claim 8, wherein the second photocurable resin includes an acrylate monomer which has three or more functional groups, and a value of a molecular weight of the acrylate monomer divided by a number of the functional groups of the acrylate monomer is equal to or more than 473.

18. The synthetic polymer film of claim 12, wherein the first surface is included in the third portion.

19. The synthetic polymer film of claim 12, wherein the third portion includes no urethane acrylate structure.

20. The synthetic polymer film of claim 12, wherein the fluorine content is higher in the third portion than in the fourth portion, and the second portion does not include any fluorine element.

21. The synthetic polymer film of claim 12, wherein the acryloyl group-containing monomer comprises acryloylmorpholine.

* * * * *